United States Patent
Brucelle et al.

(10) Patent No.: US 11,013,718 B2
(45) Date of Patent: *May 25, 2021

(54) LSD1 INHIBITORS AND MEDICAL USES THEREOF

(71) Applicant: Constellation Pharmaceuticals, Inc., Cambridge, MA (US)

(72) Inventors: Francois Brucelle, Cambridge, MA (US); Victor S. Gehling, Somerville, MA (US); Avinash Khanna, Cambridge, MA (US)

(73) Assignee: Constellation Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/671,559

(22) Filed: Nov. 1, 2019

(65) Prior Publication Data

US 2020/0306223 A1 Oct. 1, 2020

Related U.S. Application Data

(63) Continuation of application No. 16/345,011, filed as application No. PCT/US2017/058405 on Oct. 26, 2017, now Pat. No. 10,517,849.

(60) Provisional application No. 62/413,166, filed on Oct. 26, 2016, provisional application No. 62/413,162, filed on Oct. 26, 2016.

(51) Int. Cl.
| | |
|---|---|
| C07D 205/12 | (2006.01) |
| A61K 31/397 | (2006.01) |
| A61P 31/22 | (2006.01) |
| A61P 31/18 | (2006.01) |
| A61P 35/02 | (2006.01) |
| A61K 31/438 | (2006.01) |
| C07D 221/20 | (2006.01) |
| A61P 35/00 | (2006.01) |

(52) U.S. Cl.
CPC .......... *A61K 31/397* (2013.01); *A61K 31/438* (2013.01); *A61P 31/18* (2018.01); *A61P 31/22* (2018.01); *A61P 35/00* (2018.01); *A61P 35/02* (2018.01); *C07D 205/12* (2013.01); *C07D 221/20* (2013.01)

(58) Field of Classification Search
CPC .................................................. C07D 205/12
See application file for complete search history.

(56) References Cited

U.S. PATENT DOCUMENTS

| | | | |
|---|---|---|---|
| 4,639,273 A | 1/1987 | Gilmore et al. | |
| 5,188,927 A | 2/1993 | Okada et al. | |
| 5,344,467 A | 9/1994 | Huang et al. | |
| 5,424,293 A | 6/1995 | Zoller et al. | |
| 5,554,594 A | 9/1996 | Zoller et al. | |
| 6,518,444 B1 | 2/2003 | McConville et al. | |
| 7,135,437 B2 | 11/2006 | Pallas et al. | |
| 7,172,703 B2 | 2/2007 | Javora et al. | |
| 7,285,607 B2 | 10/2007 | Blann et al. | |
| 7,507,485 B2 | 3/2009 | Oh et al. | |
| 7,678,281 B2 | 3/2010 | Javora et al. | |
| 8,877,832 B2 | 11/2014 | Ito et al. | |
| 8,992,932 B2 | 3/2015 | Lerchen et al. | |
| 9,315,488 B2 | 4/2016 | Ding et al. | |
| 10,517,849 B2 | 12/2019 | Brucelle et al. | |
| 10,526,287 B2 | 1/2020 | Albrecht et al. | |
| 2003/0087764 A1 | 5/2003 | Pallas et al. | |
| 2003/0096708 A1 | 5/2003 | Agbaje et al. | |
| 2003/0118866 A1 | 6/2003 | Oh et al. | |
| 2004/0034015 A1 | 2/2004 | Robichaud et al. | |
| 2004/0043983 A1 | 3/2004 | Li | |

(Continued)

FOREIGN PATENT DOCUMENTS

| | | |
|---|---|---|
| AU | 2005266890 A1 | 2/2006 |
| CN | 102947285 A | 2/2013 |

(Continued)

OTHER PUBLICATIONS

Alford et al., Expanding the scope of donor/acceptor carbenes to N-phthalimido donor groups: diastereoselective synthesis of 1-cyclopropane a-amino acids. Org Lett. Dec. 7, 2012;14(23):6020-3.

(Continued)

*Primary Examiner* — Laura L Stockton

(74) *Attorney, Agent, or Firm* — McCarter & English, LLP; Steven G. Davis; Michael J. DeGrazia

(57) ABSTRACT

Provided are novel compounds of Formula (I or Ia'): and pharmaceutically acceptable salts thereof, which are useful for treating a variety of diseases, disorders or conditions, associated with LSD1. Also provided are pharmaceutical compositions comprising the novel compounds of Formula (I or Ia'), pharmaceutically acceptable salts thereof, and methods for their use in treating one or more diseases, disorders or conditions, associated with LSD1.

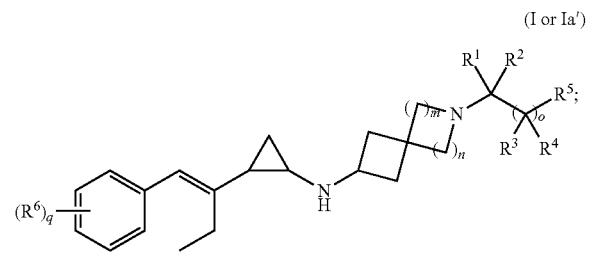

18 Claims, 2 Drawing Sheets

(56) References Cited

U.S. PATENT DOCUMENTS

| | | |
|---|---|---|
| 2004/0043985 A1 | 3/2004 | Hicks et al. |
| 2004/0127482 A1 | 7/2004 | Robichaud et al. |
| 2005/0227875 A1 | 10/2005 | Javora et al. |
| 2006/0020091 A1 | 1/2006 | Blann et al. |
| 2007/0027178 A1 | 2/2007 | Lee |
| 2007/0049613 A1 | 3/2007 | Chen et al. |
| 2007/0138101 A1 | 6/2007 | Javora et al. |
| 2010/0055169 A1 | 3/2010 | Dande et al. |
| 2012/0190770 A1 | 7/2012 | Ito et al. |
| 2013/0095123 A1 | 4/2013 | Lerchen et al. |
| 2015/0057326 A1 | 2/2015 | Wu |
| 2015/0069342 A1 | 3/2015 | Lee et al. |
| 2015/0069344 A1 | 3/2015 | Kim et al. |
| 2015/0069347 A1 | 3/2015 | Kim et al. |
| 2015/0069355 A1 | 3/2015 | Hwang et al. |
| 2015/0221878 A1 | 8/2015 | Rai et al. |
| 2015/0239918 A1 | 8/2015 | Johnson et al. |
| 2020/0069677 A1* | 3/2020 | McGrath ............... A61K 31/20 |

FOREIGN PATENT DOCUMENTS

| | | |
|---|---|---|
| DE | 10302781 A1 | 9/2003 |
| DE | 102012001247 A1 | 7/2012 |
| EP | 461670 A1 | 12/1991 |
| EP | 580008 A2 | 1/1994 |
| EP | 584694 A1 | 3/1994 |
| EP | 678786 A1 | 10/1995 |
| EP | 2433940 A1 | 3/2012 |
| JP | 2003-064035 A | 3/2003 |
| JP | 2004-189893 A | 7/2004 |
| JP | 2008-207466 A | 9/2008 |
| JP | 2010-126651 A | 6/2010 |
| JP | 47-89966 B2 | 10/2011 |
| JP | 2012-077108 A | 4/2012 |
| JP | 2014-232188 A | 12/2014 |
| JP | 2015-030699 A | 2/2015 |
| WO | 1987/07637 A2 | 12/1987 |
| WO | 1992/17456 A1 | 10/1992 |
| WO | 1992/20762 A1 | 11/1992 |
| WO | 1992/20765 A1 | 11/1992 |
| WO | 1993/16684 A1 | 9/1993 |
| WO | 1997/01545 A1 | 1/1997 |
| WO | 1997/29825 A1 | 8/1997 |
| WO | 2000/069828 A1 | 11/2000 |
| WO | 2001/010822 A1 | 2/2001 |
| WO | 2001/089302 A2 | 11/2001 |
| WO | 2002/000623 A1 | 1/2002 |
| WO | 2002/021924 A2 | 3/2002 |
| WO | 2002/050088 A1 | 6/2002 |
| WO | 2002/096199 A2 | 12/2002 |
| WO | 2002/102153 A2 | 12/2002 |
| WO | 2003/003008 A1 | 1/2003 |
| WO | 2004/018436 A2 | 3/2004 |
| WO | 2004/019681 A2 | 3/2004 |
| WO | 2004/052862 A1 | 6/2004 |
| WO | 2004/078686 A1 | 9/2004 |
| WO | 2005/040135 A1 | 5/2005 |
| WO | 2005/105734 A1 | 11/2005 |
| WO | 2005/118543 A1 | 12/2005 |
| WO | 2005/123884 A2 | 12/2005 |
| WO | 2006/024783 A1 | 3/2006 |
| WO | 2006/032926 A2 | 3/2006 |
| WO | 2006/037335 A2 | 4/2006 |
| WO | 2006/038594 A1 | 4/2006 |
| WO | 2007/033002 A1 | 3/2007 |
| WO | 2007/044100 A1 | 4/2007 |
| WO | 2007/071396 A2 | 6/2007 |
| WO | 2007/116011 A2 | 10/2007 |
| WO | 2008/104994 A2 | 9/2008 |
| WO | 2009/067797 A1 | 6/2009 |
| WO | 2009/087225 A2 | 7/2009 |
| WO | 2009/105782 A1 | 8/2009 |
| WO | 2009/121486 A1 | 10/2009 |
| WO | 2010/007317 A1 | 1/2010 |
| WO | 2010/129687 A1 | 11/2010 |
| WO | 2010/148422 A1 | 12/2010 |
| WO | 2010/148652 A1 | 12/2010 |
| WO | 2011/039403 A1 | 4/2011 |
| WO | 2011/068561 A1 | 6/2011 |
| WO | 2012/016188 A2 | 2/2012 |
| WO | 2012/020215 A1 | 2/2012 |
| WO | 2012/146338 A1 | 11/2012 |
| WO | 2012/178123 A1 | 12/2012 |
| WO | 2012/178124 A1 | 12/2012 |
| WO | 2012/178125 A1 | 12/2012 |
| WO | 2013/005057 A1 | 1/2013 |
| WO | 2013/014207 A1 | 1/2013 |
| WO | 2013/045516 A1 | 4/2013 |
| WO | 2013/049686 A1 | 4/2013 |
| WO | 2013/057320 A1 | 4/2013 |
| WO | 2013/068075 A1 | 5/2013 |
| WO | 2013/168103 A1 | 11/2013 |
| WO | 2014/045031 A1 | 3/2014 |
| WO | 2014/052896 A1 | 4/2014 |
| WO | 2014/057095 A1 | 4/2014 |
| WO | 2014/065083 A1 | 5/2014 |
| WO | 2014/068893 A1 | 5/2014 |
| WO | 2014/157267 A1 | 10/2014 |
| WO | 2014/210564 A1 | 12/2014 |
| WO | 2015/014986 A1 | 2/2015 |
| WO | 2015/024120 A1 | 2/2015 |
| WO | 2015/126357 A1 | 8/2015 |
| WO | 2015/133247 A1 | 9/2015 |
| WO | 2016/172496 A1 | 10/2016 |

OTHER PUBLICATIONS

Bennani-Baiti et al., Lysine-specific demethylase 1 (LSD1/KDM1A/AOF2/BHC110) is expressed and is an epigenetic drug target in chondrosarcoma, Ewing's sarcoma, osteosarcoma, and rhabdomyosarcoma. Hum Pathol. Aug. 2012;43(8):1300-7.

Cai et al., Androgen receptor gene expression in prostate cancer is directly suppressed by the androgen receptor through recruitment of lysine-specific demethylase 1. Cancer Cell. Oct. 18, 2011;20(4):457-71.

Hayami et al., Overexpression of LSD1 contributes to human carcinogenesis through chromatin regulation in various cancers. Int J Cancer Feb. 1, 2011;128(3):574-86.

Konovalov et al., Analysis of the levels of lysine-specific demethylase 1 (LSD1) mRNA in human ovarian tumors and the effects of chemical LSD1 inhibitors in ovarian cancer cell lines. Journal of Ovarian Research. 2013;6:75. 15 pages.

Lian et al., Inhibition of lysine-specific histone demethylase LSD1 suppresses melanoma growth. FASEB J. Apr. 1, 2013;27(1 supplemental).

Liang et al., A novel selective LSD1/KDM1A inhibitor epigenetically blocks herpes simplex virus lytic replication and reactivation from latency. MBio. Feb. 5, 2013;4(1):e00558-12.

Lynch et al., LSD1 Inhibition: A Therapeutic Strategy in Cancer? Expert Opin Ther Targets. 16(12):1239-49 (2012).

McMahon, VEGF receptor signaling in tumor angiogenesis. The Oncologist. 2000;5 Suppl 1:3-10.

Neidle, Failure Modes in the Discovery Process. Cancer Drug Design and Discovery. Elsevier/Academic Press. pp. 427-431, (2008).

Northcott et al., Enhancer hijacking activates GFI1 family oncogenes in medulloblastoma. Nature. Jul. 24, 2014;511(7510):428-34.

Pajtler et al., The KDM1A histone demethylase is a promising new target for the epigenetic therapy of medulloblastoma. Acta Neuropathol Commun. May 29, 2013;1:19.

Pinedo et al., Translational Research: the Role of VEGF in Tumor Angiogenesis. The Oncologist. 2000;5 Suppl 1:1-2.

Przespolewski et al., Inhibitors of LSD1 as a Potential Therapy for Acute Myeloid Leukemia. Expert Opin Investig Drugs. 25(7):771-80 (2016).

Sakane et al., Activation of HIV transcription by the viral Tat protein requires a demethylation step mediated by lysine-specific demethylase 1 (LSD1/KDM1). PLoS Pathog. Aug. 2011;7(8):e1002184.

Stazi et al., LSD1 Inhibitors: A Patent Review (2010-2015). Expert Opin Ther Pat. 26(5):565-80 (2016).

(56) References Cited

OTHER PUBLICATIONS

Willmann et al., Impairment of prostate cancer cell growth by a selective and reversible lysine-specific demethylase 1 inhibitor. Int J Cancer. Dec. 1, 2012;131(11):2704-9.
Yokoyama et al., Transrepressive function of TLX requires the histone demethylase LSD1. Mol Cell Biol. Jun. 2008;28(12):3995-4003.
Yu et al., High expression of lysine-specific demethylase 1 correlates with poor prognosis of patients with esophageal squamous cell carcinoma. Biochem Biophys Res Commun. Jul. 26, 2013;437(2):192-8.
Zhang et al., Pluripotent Stem Cell Protein Sox2 Confers Sensitivity to LSD1 Inhibition in Cancer Cells. Cell Reports 2013;5:1-13.

* cited by examiner

LSD1 INHIBITORS AND MEDICAL USES THEREOF

RELATED APPLICATIONS

This application is a continuation of U.S. patent application Ser. No. 16/345,011, filed Apr. 25, 2019, which is a 35 U.S.C. § 371 national stage filing International Application No. PCT/US2017/058405, filed Oct. 26, 2017, which claims priority to U.S. Provisional Application No. 62/413,162, filed Oct. 26, 2016 and U.S. Provisional Application No. 62/413,166, filed Oct. 26, 2016, the contents of each of which are incorporated herein by reference.

BACKGROUND

Lysine-specific demethylase (LSD1), also known as lysine (K)-specific demethylase 1A (LSD1), is a protein in humans that in encoded by the KDM1A gene and specifically demethylates mono- or dimethylated histone H3 lysine4 (H3K4) and H3 lysine 9 (H3K9) via a redox process. Biochimica et Biophysica Acta 1829 (2013) 981-986. LSD1 has been found to possess oncogenic properties in several cancers ranging from prostate (Cancer Res., 66 (2006), pp. 11341-11347) bladder (Mol. Carcinog., 50 (2011), pp. 931-944) neuroblastomas, (Cancer Res., 69 (2009), pp. 2065-2071) lung cancers, (PLoS One, 7 (2012), p. e35065) sarcomas and hepato-carcinomas (Tumour Biol. (2012). LSD1 pharmacological inhibitors have been shown e.g., to treat leukemias (Nat. Med., 18 (2012), pp. 605-611) and also solid tumors (Tumour Biol. (2012)).

SUMMARY

It has now been found that compounds of structural Formula:

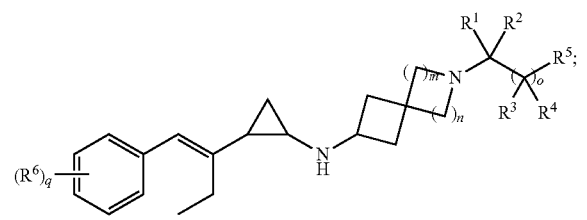

or a pharmaceutically acceptable salt thereof, and compositions comprising compounds of this Formula, wherein each of $R^1$, $R^2$, $R^3$, $R^4$, $R^5$, $R^6$, m, n, o, and q are defined and described herein, are effective inhibitors of LSD1. See Table 6 in the Exemplification Section below. Conditions treated by the disclosed compounds are described herein.

DETAILED DESCRIPTION OF CERTAIN EMBODIMENTS

1. General Description of Compounds

Figure 1:
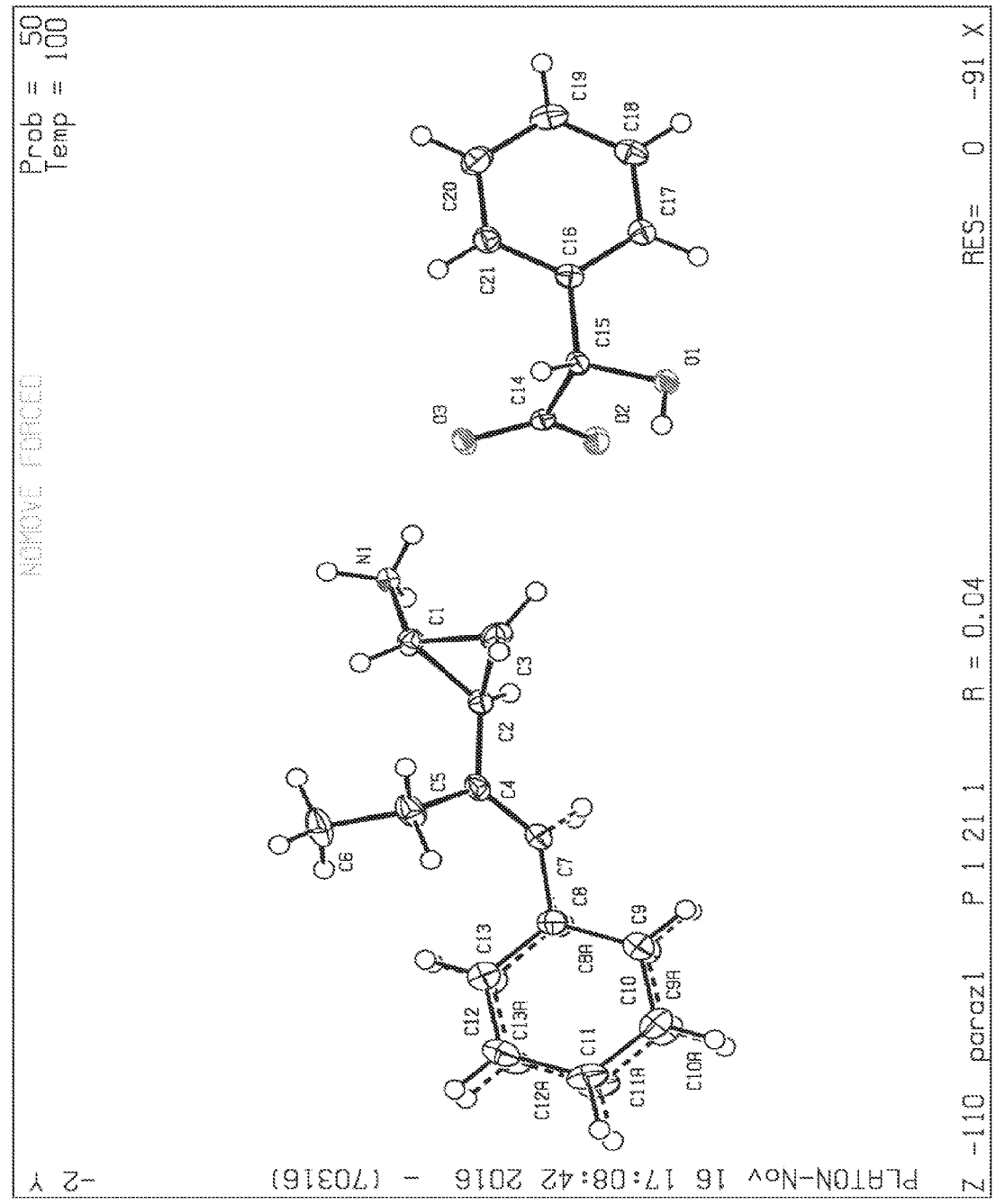
FIG. 1 depicts the X-ray crystal structure for intermediate (1R,2S)-2-((E)-1-phenylbut-1-en-2-yl)cyclopropan-1-amine (S)-2-hydroxy-2-phenylacetate.

In certain embodiments, the present disclosure provides a compound of Formula I:

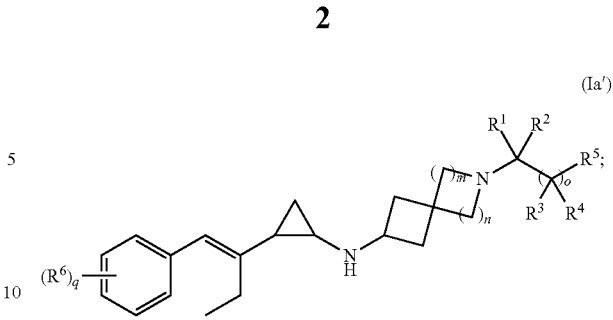

or a pharmaceutically acceptable salt thereof, wherein
n is 1 or 2;
m is 1 or 2;
o is 0 or 1;
q is 1, 2, or 3;
$R^1$ is hydrogen or ($C_1$-$C_6$)alkyl;
$R^2$ is hydrogen or ($C_1$-$C_6$)alkyl optionally substituted with OH or ($C_1$-$C_6$)alkoxy;
$R^3$ and $R^4$, if present are each independently selected from hydrogen, halo, OH, and ($C_1$-$C_6$)alkyl;
$R^5$ is selected from $NH_2$, —NH($SO_2$)($C_1$-$C_6$)alkyl, —NH($SO_2$)($C_1$-$C_6$)alkylO($C_1$-$C_6$)alkyl, —NHC(O)($C_1$-$C_6$)alkyl, —NH($SO_2$)($C_3$-$C_6$)cycloalkyl, OH, —O($C_1$-$C_6$)alkyl, —$SO_2NH_2$, —C(O)$NH_2$, —C(O)NH($C_1$-$C_6$)alkyl, —C(O)N[($C_1$-$C_6$)alkyl]$_2$, —C(O)NH($SO_2$)($C_1$-$C_6$)alkyl, —C(O)NH($C_1$-$C_6$)alkyl($SO_2$)($C_1$-$C_6$)alkyl, —C(O)NH($SO_2$)($C_3$-$C_6$)cycloalkyl, —C(O)NH($C_1$-$C_6$)alkylOH, —C(O)NH($C_1$-$C_6$)alkylO($C_1$-$C_6$)alkyl, and ($C_1$-$C_4$)alkyl substituted with OH; and
$R^6$ is selected from ($C_1$-$C_6$)alkyl, halo($C_1$-$C_6$)alkyl, ($C_1$-$C_6$)alkoxy, halo($C_1$-$C_6$)alkoxy, halo, and cyano.

In certain embodiments, the present disclosure provides a compound of Formula Ia':

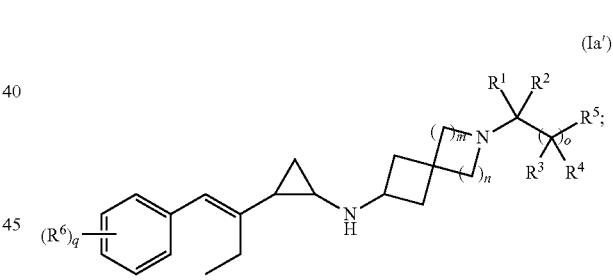

or a pharmaceutically acceptable salt thereof, wherein
n is 1 or 2;
m is 1 or 2;
o is 0 or 1;
q is 0, 1, 2, or 3;
$R^1$ is hydrogen or ($C_1$-$C_6$)alkyl;
$R^2$ is hydrogen or ($C_1$-$C_6$)alkyl optionally substituted with OH or ($C_1$-$C_6$)alkoxy;
$R^3$ and $R^4$, if present are each independently selected from hydrogen, halo, OH, and ($C_1$-$C_6$)alkyl;
$R^5$ is selected from $NH_2$, —NH($SO_2$)($C_1$-$C_6$)alkyl, —NH($SO_2$)($C_1$-$C_6$)alkylO($C_1$-$C_6$)alkyl, —NHC(O)($C_1$-$C_6$)alkyl, —NH($SO_2$)($C_3$-$C_6$)cycloalkyl, OH, —O($C_1$-$C_6$)alkyl, —$SO_2NH_2$, —C(O)$NH_2$, —C(O)NH($C_1$-$C_6$)alkyl, —C(O)N[($C_1$-$C_6$)alkyl]$_2$, —C(O)NH($SO_2$)($C_1$-$C_6$)alkyl, —C(O)NH($C_1$-$C_6$)alkyl($SO_2$)($C_1$-$C_6$)alkyl, —C(O)NH($SO_2$)($C_3$-$C_6$)cycloalkyl, —C(O)NH($C_1$-$C_6$)alkylOH, —C(O)NH($C_1$-$C_6$)alkylO($C_1$-$C_6$)alkyl, and ($C_1$-$C_4$)alkyl substituted with OH; and $R^6$, if present, is selected from $(C_1-C_6)$alkyl, halo$(C_1-C_6)$alkyl, $(C_1-C_6)$alkoxy, halo$(C_1-C_6)$alkoxy, halo, and cyano.

2. Compounds and Definitions

The terms "halo" and "halogen" as used herein refer to an atom selected from fluorine (fluoro, F), chlorine (chloro-, Cl), bromine (-bromo, Br), and iodine (iodo-, -I).

The term "alkyl" used alone or as part of a larger moiety, such as "alkoxy", "haloalkyl", and the like, means saturated straight-chain or branched monovalent hydrocarbon radical. Unless otherwise specified, an alkyl group typically has 1-6 carbon atoms, i.e., $(C_1-C_6)$alkyl. As used herein, a "$(C_1-C_6)$ alkyl" group is means a radical having from 1 to 6 carbon atoms in a linear or branched arrangement.

The term "haloalkyl" includes mono, poly, and perhaloalkyl groups where the halogens are independently selected from fluorine, chlorine, bromine, and iodine.

"Alkoxy" means an alkyl radical attached through an oxygen linking atom, represented by —O-alkyl. For example, "$(C_1-C_4)$alkoxy" includes methoxy, ethoxy, proproxy, and butoxy.

When used in connection to describe a chemical group that may have multiple points of attachment, a hyphen (-) designates the point of attachment of that group to the variable to which is is defined. For example, —NH(SO₂)($C_3-C_6$)cycloalkyl means that the point of attachment for this group is on the nitrogen atom.

The disclosed compounds exist in various stereoisomeric forms. Stereoisomers are compounds that differ only in the spatial arrangement of their atoms. Different spatial arrangements in a compound can result from e.g., the orientation of four different substituents around a chiral carbon atom (i.e., a chiral center), the orientation of two or more substituents around a double bond, or the orientation of two or more substituents on a cycloalkyl ring.

Enantiomers are one type of stereoisomer that can arise from a chiral center or chiral centers. Enantiomers are pairs of stereoisomers whose mirror images are not superimposable, most commonly because they contain an asymmetrically substituted carbon atom or carbon atoms that acts as a chiral center(s). "R" and "S" represent the absolute configuration of substituents around one or more chiral carbon atoms, where each chiral center is assigned the prefix "R" or "S" according to whether the chiral center configuration is right- (clockwise rotation) or left-handed (counter clockwise rotation). If the turn is clockwise or right-handed about a chiral carbon, the designation is "R" for rectus. If the turn is counter clockwise or left-handed about a chiral carbon, the designation is "S" for sinister.

Enantiomeric purity reflects the degree to which one enantiomer of a compound is predominantly present over the other enantiomer of that compound. It is determined by subtracting the percent composition of the major enantiomer with the percent composition of the minor enantiomer that is present. For example, a racemic mixture has an enantiomeric purity of 0%, while a single completely pure enantiomer has an enantiomeric purity of 100%. A composition with 70% of one enantiomer and 30% of the other has an enantiomeric purity of 40% (70%-30%).

Diastereomers are stereoisomers that are not related as object and mirror image and are not enantiomers. Unlike enantiomers which are mirror images of each other and non-superimposable, diastereomers are not mirror images of each other and non-superimposable. Diastereomers have two or more chiral centers.

Geometric isomers arise when two or more substituents on a double bond or ring can have different spatial orientations with respect to one another due to the presence of the double bond or ring structure. When the orientation of the substituents of a geometric isomer are on opposite sides of the double bond, those substituents are said to be "trans" to one another or denoted by the letter "E." When the orientation of the substituents of a geometric isomer are on the same side of the double bond, those substituents are said to be "cis" to one another or denoted by the letter "Z."

When the configuration of two or more substituents about a double bond is indicated by structure; by "E" or "Z" designations; by "cis" or "trans"; or by a combination of the foregoing, it is to be understood that the depicted stereochemical purity with respect to that double bond is at least 85%, at least 90%, at least 95%, at least 97%, at least 98% or at least 99% by weight. Stereochemical purity by weight with respect to a double bond means the percent by weight of the compound in a composition having the indicated stereochemistry about the double bond. For example, in compounds having the Formula I or Ia', when the double bond is represented by

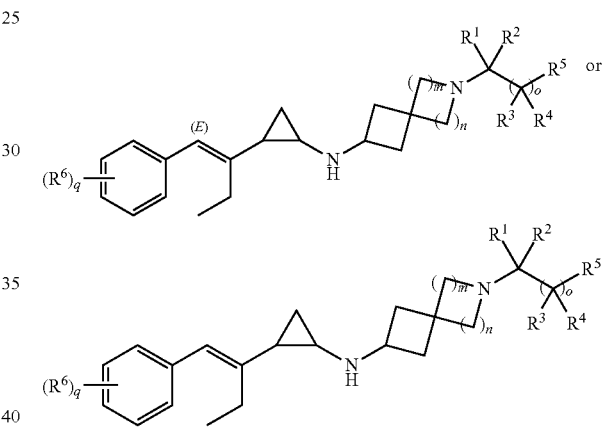

it is to be understood that the compound has a stereochemical purity with respect to the depicted trans (E) stereochemistry about the double bond, i.e., at least 85%, at least 90%, at least 95%, at least 97%, at least 98% or at least 99% by weight of the compound in a composition contains the represented trans (i.e., E) double bond.

Geometric isomers can also arise based on the orientation of two or more substituents about a cyclic group. For example, in compounds of Formula I or Ia', the orientation of

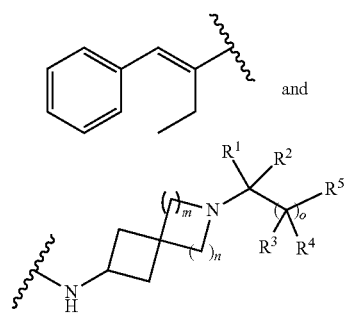

about the cyclopropyl can give rise to two different cis configurations (as in

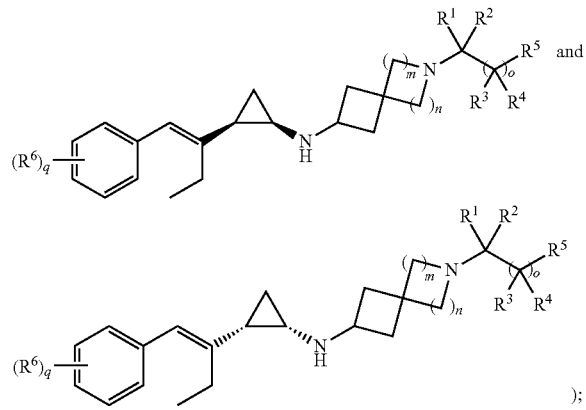

and two different trans configurations (as in

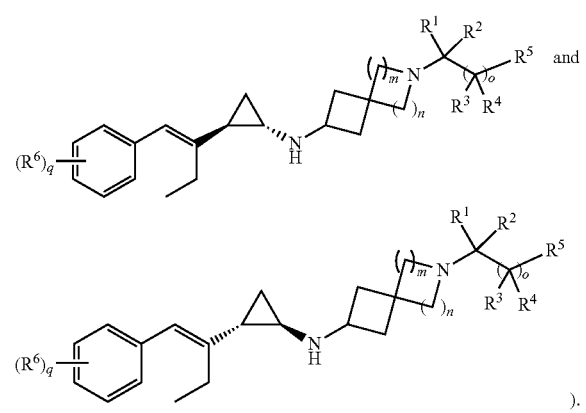

).

In instances where the stereochemistry about the cyclopropyl is not defined, as in

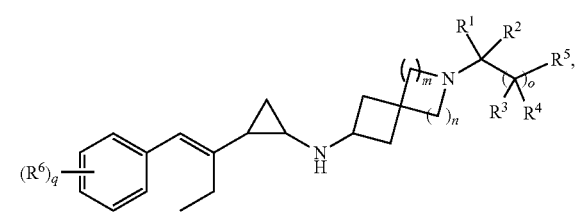

the structure includes one of the cis or trans isomers free of other cis and trans stereoisomers, or, alternatively, any mixture of cis and trans stereoisomers.

When the stereochemistry about the cyclopropyl in the compounds of Formula I or Ia' is indicated by structure only, the structure is meant to depict the relative stereochemistry at one of the chiral centers in the cyclopropyl relative to the stereochemistry at the other chiral center, and not the absolute stereochemistry at either chiral center in the cyclopropyl. For example, when the stereochemistry about the cyclopropyl is depicted by structure only as being trans, the stereochemical purity of the compound with respect to the depicted trans configuration about the cyclopropyl is at least 85%, at least 90%, at least 95%, at least 97%, at least 98% or at least 99% by weight, i.e., the percent by weight of the compound in the composition having the trans stereochemistry at the cyclopropyl is at least 85%, at least 90%, at least 95%, at least 97%, at least 98% or at least 99% by weight. For example, a compound represented by the formula:

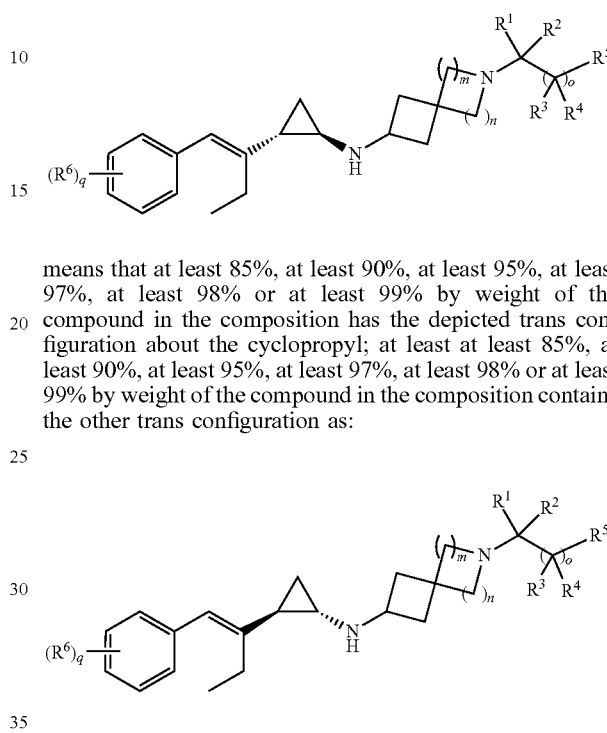

means that at least 85%, at least 90%, at least 95%, at least 97%, at least 98% or at least 99% by weight of the compound in the composition has the depicted trans configuration about the cyclopropyl; at least at least 85%, at least 90%, at least 95%, at least 97%, at least 98% or at least 99% by weight of the compound in the composition contains the other trans configuration as:

or at least 85%, at least 90%, at least 95%, at least 97%, at least 98% or at least 99% by weight of the compound in the composition is a mixture of the two trans configurations.

When the absolute stereochemistry of chiral centers in a compound are indicated structurally and by "R" or "S" designations, it is to be understood that the depiction means the depicted stereoisomer at a stereochemical purity of at least 85%, at least 90%, at least 95%, at least 97%, at least 98% or at least 99% by weight, i.e., the percent by weight of the indicated stereoisomer of the compound in the composition. For example, a compound of Formula I or Ia' represented by the formula:

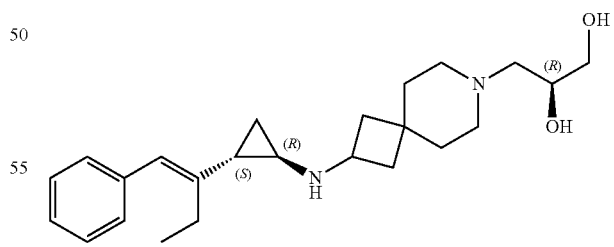

means at least 85%, at least 90%, at least 95%, at least 97%, at least 98% or at least 99% by weight of the compound of Formula I in the composition contains of the depicted stereoisomer. When the structure being depicted by structure and by "R" or "S" designation is a single enantiomer, the enantiomeric purity is at least 95% (e.g., at least 96%, at least 97%, at least 98%, at least 99%, at least 99.5%, or at least 99.9%).

When a compound is depicted by structurally without indicating the stereochemistry at a chiral center, it is to be understood that the structure includes either configuration at the chiral center or, alternatively, any mixture of configurations at that chiral center.

The 1- and 2-positions of the cyclopropyl ring represent the following:

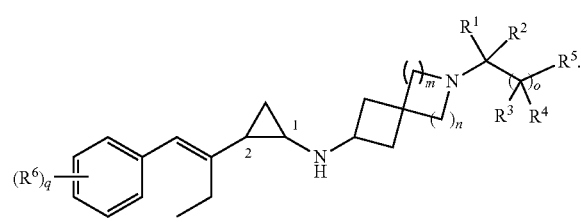

The compounds described herein may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts. Suitable pharmaceutically acceptable acid addition salts of the compounds described herein include e.g., salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include e.g., ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, benzoates and salts with amino acids such as glutamic acid.

The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

3. Description of Exemplary Compounds

In a first embodiment, the present disclosure provides a compound of Formula I or Ia':

(I or Ia')

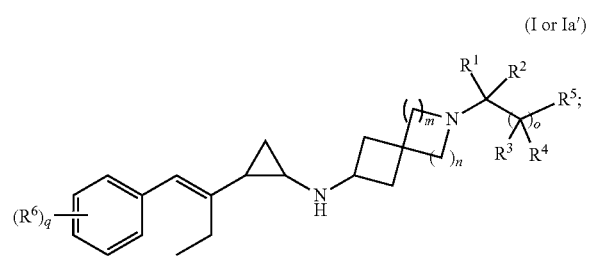

or a pharmaceutically acceptable salt thereof, wherein the variables are as described above.

In a second embodiment, the present disclosure provides a compound of Formula Ia:

(Ia)

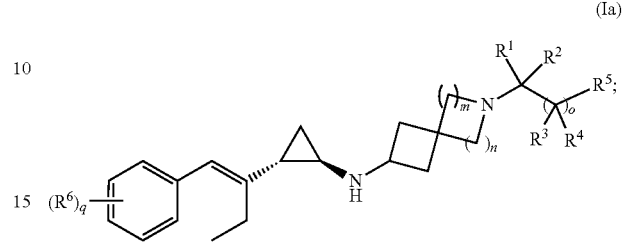

or a pharmaceutically acceptable salt thereof, wherein the variables are as described above.

In a third embodiment, $R^6$ in Formula I, Ia', or Ia is selected from methyl, ethyl, halomethyl, haloethyl, methoxy, halomethoxy, halo, and cyano, wherein the remaining variables are as described in Formula I, Ia', or the second embodiment.

In a fourth embodiment, the compound of Formula I, Ia', or Ia is of the Formula II:

(II)

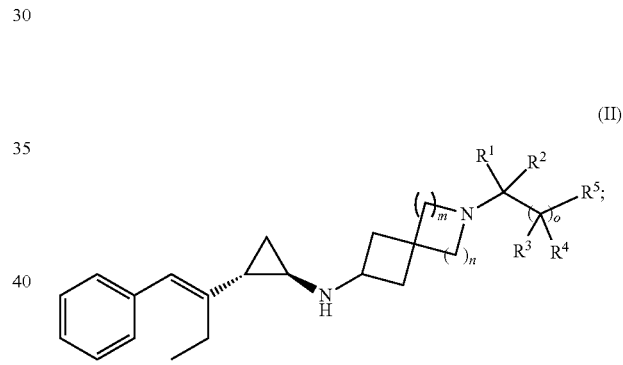

or a pharmaceutically acceptable salt thereof, wherein the remaining variables are as described in Formula I or Ia'.

In a fifth embodiment, the compound of Formula I, Ia', Ia, or II is of the Formula III:

(III)

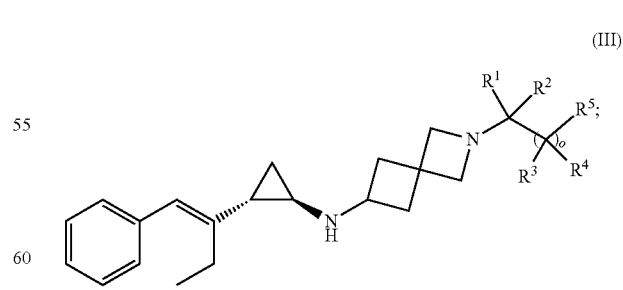

or a pharmaceutically acceptable salt thereof, wherein the remaining variables are as described in Formula I or Ia'.

In a sixth embodiment, the compound of Formula I, Ia', Ia, or II is of the Formula IV:

(IV)

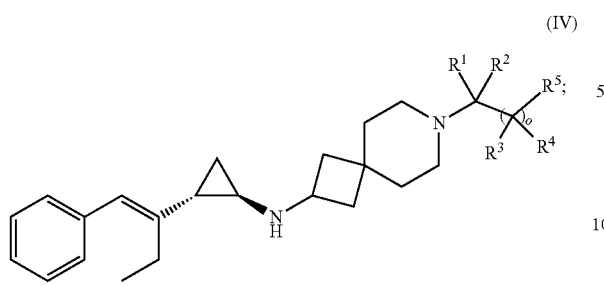

or a pharmaceutically acceptable salt thereof, wherein the remaining variables are as described in Formula I or Ia'.

In a seventh embodiment, the compound of Formula I, Ia', Ia, II, or III is of the Formula V:

(V)

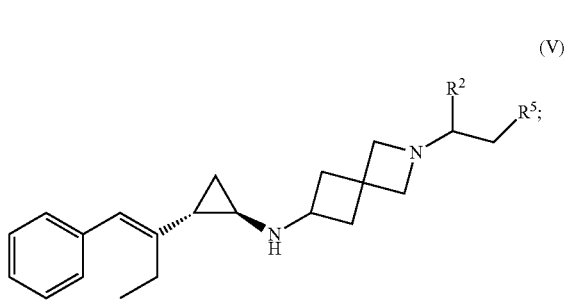

or a pharmaceutically acceptable salt thereof, wherein the remaining variables are as described in Formula I or Ia'.

In an eighth embodiment, $R^2$ in the compounds of Formula I, Ia', Ia, II, III, IV, or V is hydrogen, methyl, or hydroxy($C_1$-$C_4$)alkyl, wherein the remaining variables are as described in Formula I or in the third embodiment. Alternatively, $R^2$ in the compound of Formula I, Ia', Ia, II, III, IV, or V is hydroxy($C_1$-$C_4$)alkyl, wherein the remaining variables are as described in Formula I and the third embodiment. In another alternative, $R^2$ in the compound of Formula I, Ia', Ia, II, III, IV, or V is hydroxy($C_1$-$C_2$)alkyl, wherein the remaining variables are as described in Formula I and the third embodiment.

In a ninth embodiment, the compound of Formula I, Ia', Ia, II, or III is of the Formula:

(VI)

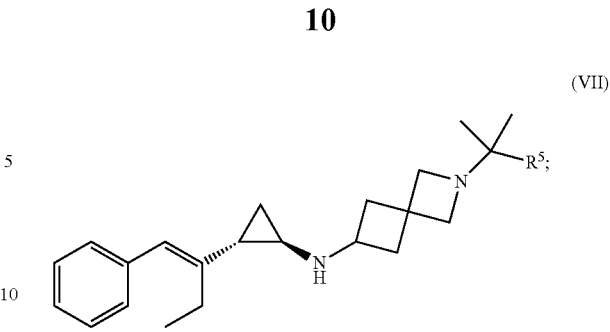

or a pharmaceutically acceptable salt thereof, wherein the remaining variables are as described in Formula I or Ia'.

In a tenth embodiment, the compound of Formula I, Ia', Ia, II, or III is of the Formula:

(VII)

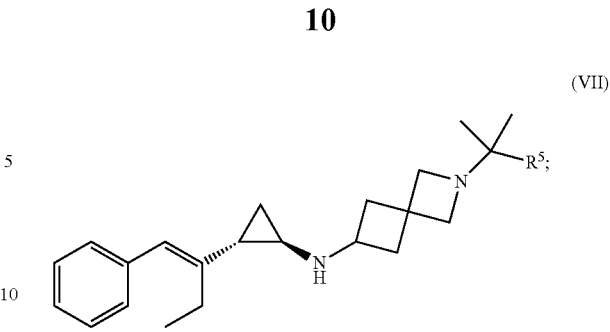

or a pharmaceutically acceptable salt thereof, wherein the remaining variables are as described in Formula I or Ia'.

In an eleventh embodiment, the compound of Formula I, Ia', Ia, II, or III is of the Formula:

(VIII)

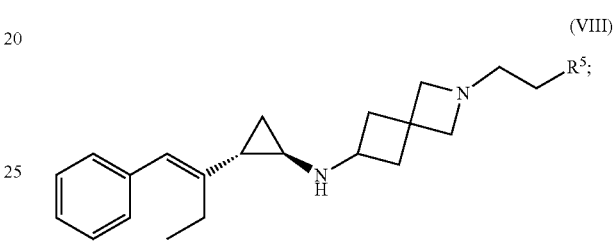

or a pharmaceutically acceptable salt thereof, wherein the remaining variables are as described in Formula I or Ia'.

In a twelfth embodiment, the compound of Formula I, Ia', Ia, II, or IV is of the Formula:

(IX)

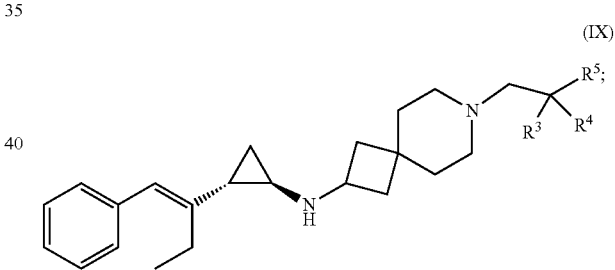

or a pharmaceutically acceptable salt thereof, wherein the remaining variables are as described in Formula I or Ia'.

In a thirteenth embodiment, the compound of Formula I, Ia', Ia, II, IV or IX is of the Formula:

(X)

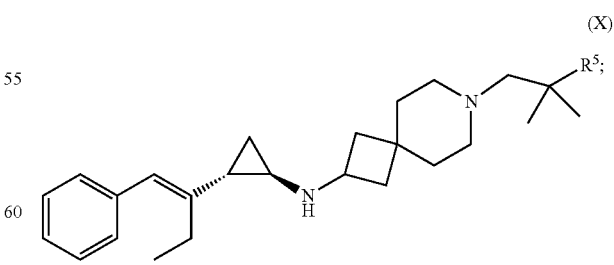

or a pharmaceutically acceptable salt thereof, wherein the remaining variables are as described in Formula I or Ia'.

In a fourteenth embodiment, the compound of Formula I, Ia', Ia, II, IV, or IX is of the Formula:

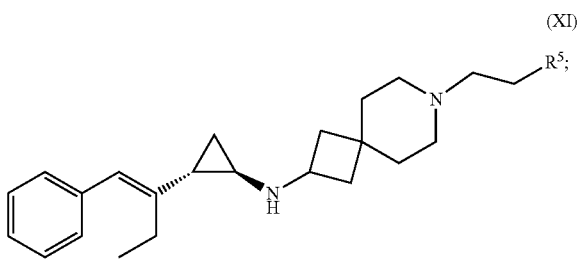

(XI)

or a pharmaceutically acceptable salt thereof, wherein the remaining variables are as described in Formula I or Ia'.

In a fifteenth embodiment, the compound of Formula I, Ia', Ia, II, IV, or IX is of the Formula:

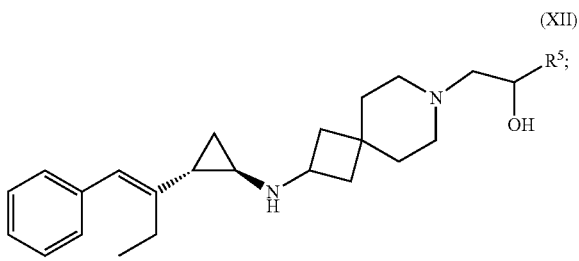

(XII)

or a pharmaceutically acceptable salt thereof, wherein the remaining variables are as described in Formula I or Ia'.

In a sixteenth embodiment, $R^5$ in any one of the compounds of Formula I, Ia', Ia, II, III, IV, V, VI, VII, VIII, IX, X, XI, or XII is $NH_2$, —$NH(SO_2)(C_1$-$C_4)$alkyl, —$NH(SO_2)(C_1$-$C_4)$alkylO$(C_1$-$C_4)$alkyl, —NHC(O)$(C_1$-$C_4)$alkyl, —NH$(SO_2)(C_3$-$C_6)$cycloalkyl, OH, —$SO_2NH_2$, —C(O)$NH_2$, —C(O)NH$(C_1$-$C_4)$alkyl, —C(O)NH$(SO_2)(C_1$-$C_4)$alkyl, —C(O)NH$(C_1$-$C_4)$alkyl$(SO_2)(C_1$-$C_4)$alkyl, —C(O)NH$(C_1$-$C_4)$alkylOH, or $(C_1$-$C_2)$alkyl substituted with OH, wherein the remaining variables are as described for Formula I or Ia' and the third or eighth embodiments. Alternatively, $R^5$ in any one of the compounds of Formula I, Ia', Ia, II, III, IV, V, VI, VII, VIII, IX, X, XI, or XII is $NH_2$, —$NH(SO_2)CH_3$, —$NH(SO_2)(CH_2)_2OCH_3$, —$NH(SO_2)CH(CH_3)_2$, —$NH(SO_2)CH_2CH_3$, —NHC(O)$CH_3$, —$NH(SO_2)$cyclopropyl, OH, —$SO_2NH_2$, —C(O)$NH_2$, —C(O)NH$(SO_2)CH_3$, —C(O)NH$(CH_3)_2$, —C(O)NHCH$(CH_3)_2$, —C(O)NHCH$_2CH_3$, —C(O)NH$(CH_2)_2(SO_2)CH_3$, —C(O)NH$(CH_2)_2OH$, or —$CH_2OH$, wherein the remaining variables are as described for Formula I or Ia', and the third or eighth embodiments. In another alternative, $R^5$ in any one of the compounds of Formula I, Ia', Ia, II, III, IV, V, VI, VII, VIII, IX, X, XI, or XII is —C(O)$NH_2$, OH, —$SO_2NH_2$, or —$NH(SO_2)CH_3$, wherein the remaining variables are as described for Formula I or Ia' and the third or eighth embodiments. In yet another alternative, $R^5$ in any one of the compounds of Formula I, Ia', Ia, II, III, IV, V, VI, VII, VIII, IX, X, XI, or XII is OH, wherein the remaining variables are as described for Formula I or Ia' and the third or eighth embodiments.

In a seventeenth embodiment, the compound of Formula Ia' is selected from from

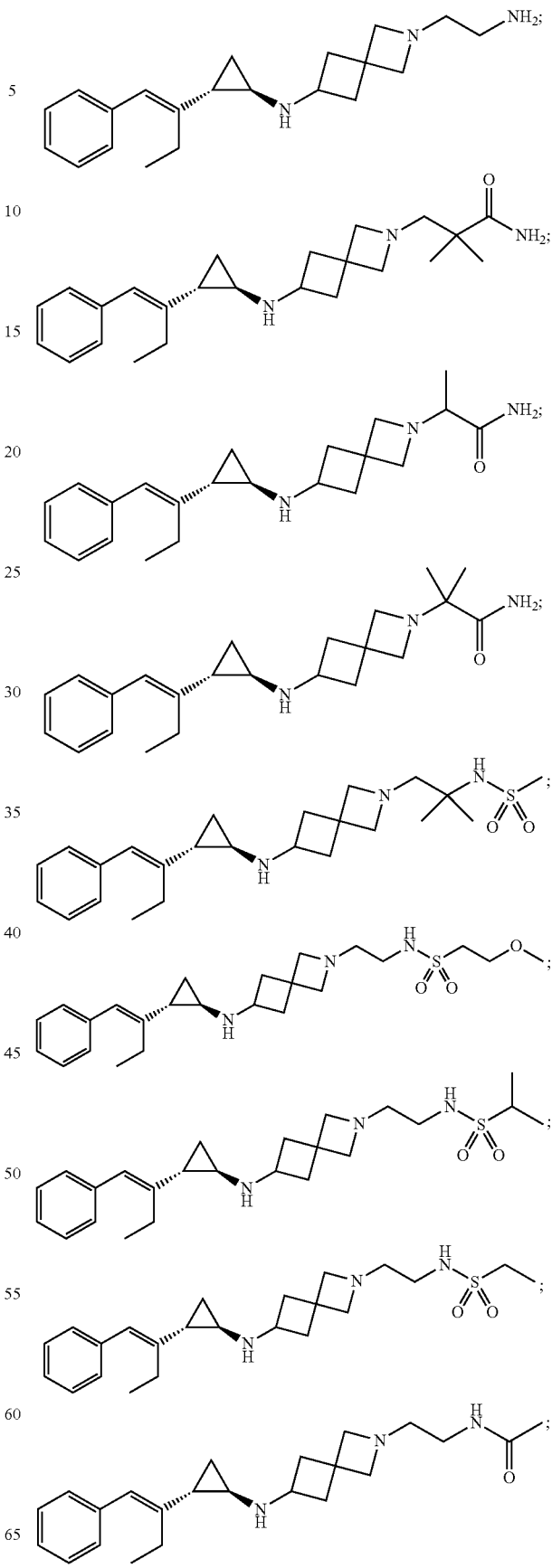

-continued
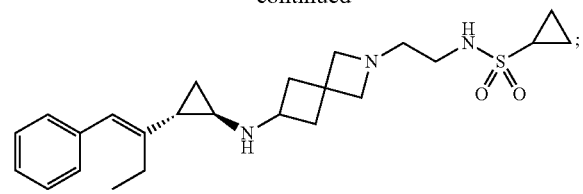
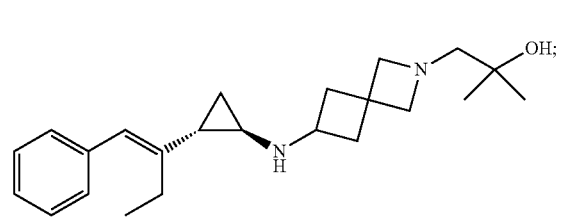
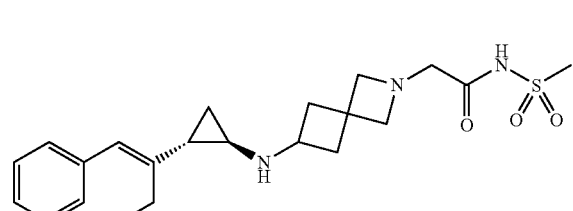
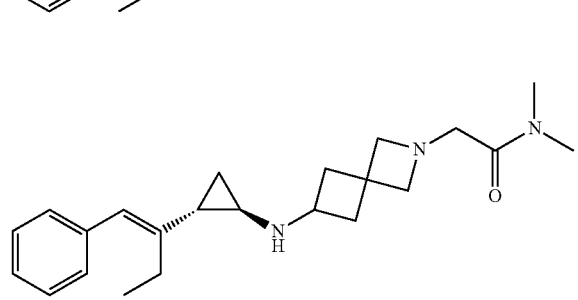
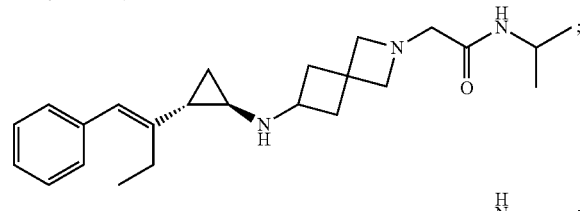
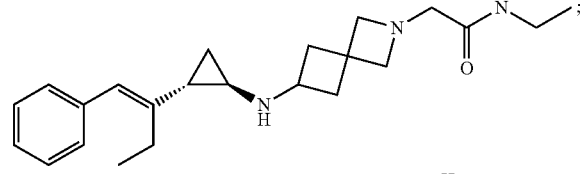
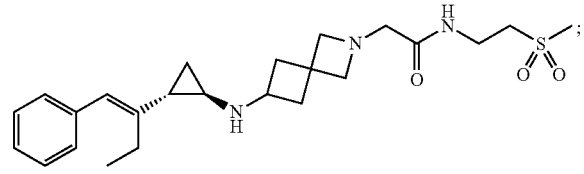
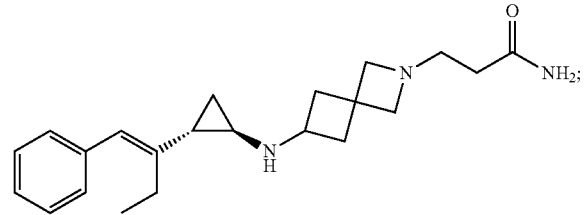
-continued
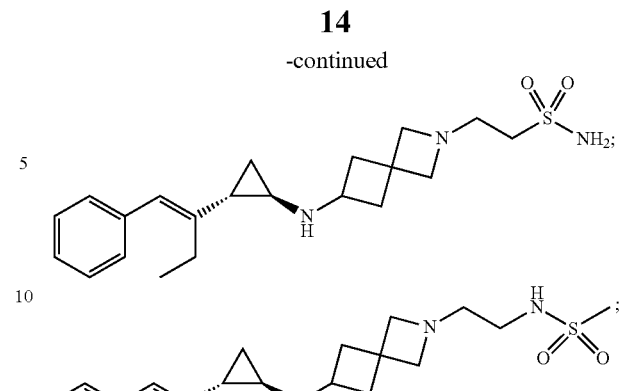
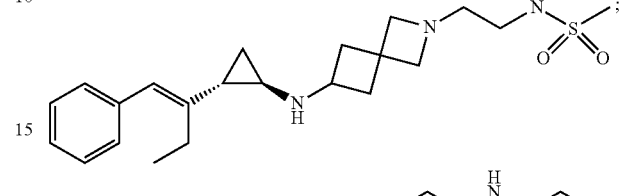
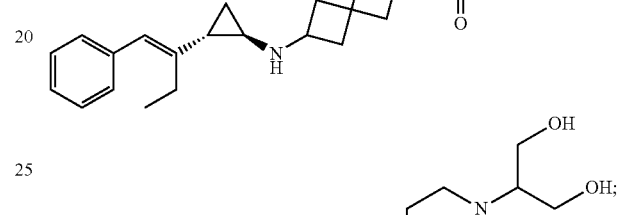
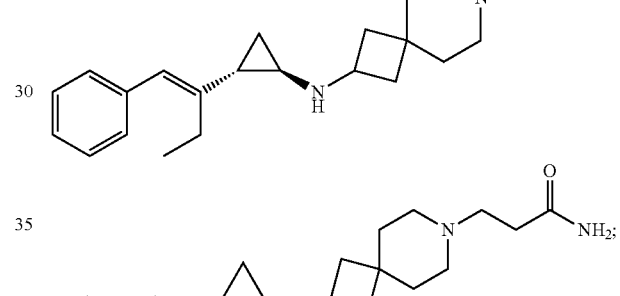
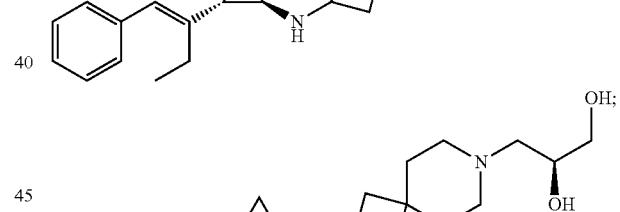
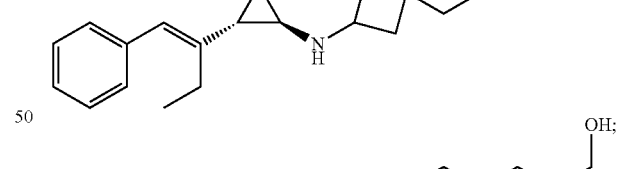
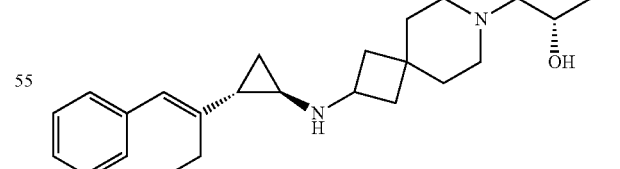
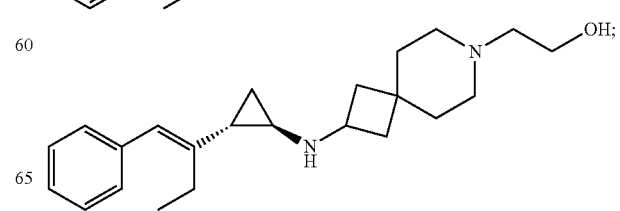

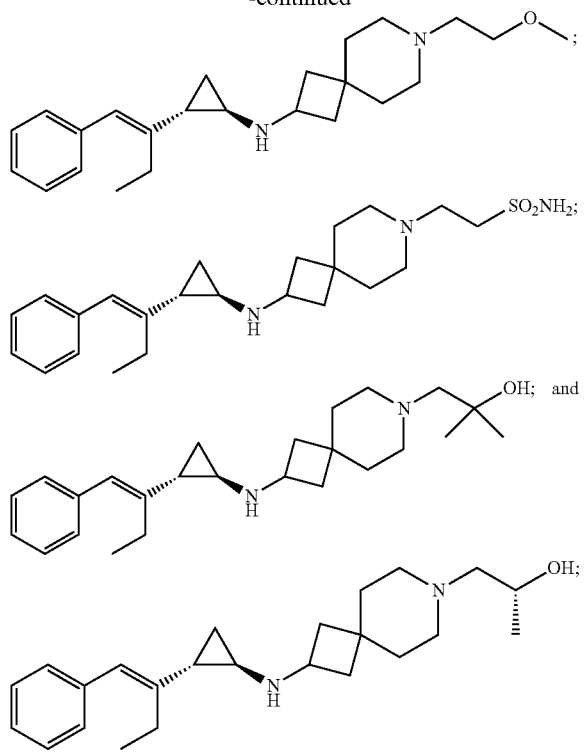

or a pharmaceutically acceptable salt thereof.

In an eighteenth embodiment, the compound of Formula Ia' is:

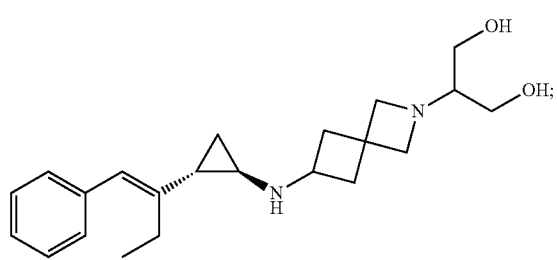 [SMILES: CC/C(=C\c1ccccc1)[C@@H]1C[C@H]1NC1CC2(C1)CN(C(CO)CO)C2]

or a pharmaceutically acceptable salt thereof.

In a nineteenth embodiment, the compound of Formula Ia' is:

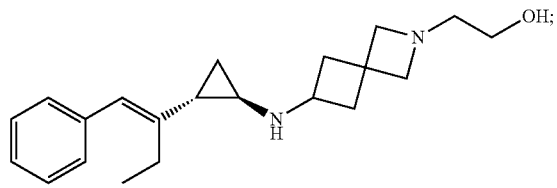 [SMILES: CC/C(=C\c1ccccc1)[C@@H]1C[C@H]1NC1CC2(C1)CN(CCO)C2]

or a pharmaceutically acceptable salt thereof.

In a twentieth embodiment, the compounds described herein (e.g., Formula I, Ia', Ia, II, III, IV, V, VI, VII, VIII, IX, X, XI, or XII and those in the seventeenth to nineteenth embodiment) are single enantiomers having an enantiomeric purity of at least 95% (e.g., at least 96%, at least 97%, at least 98%, at least 99%, at least 99.5%, or at least 99.9%).

In a twenty-first embodiment, the stereochemical configuration about the cyclopropyl ring in the compounds described herein (e.g., Formula I, Ia', Ia, II, III, IV, V, VI, VII, VIII, IX, X, XI, or XII and those in the seventeenth to nineteenth embodiment) is 1R,2S.

In a twenty-second embodiment, the stereochemical configuration about the cyclopropyl ring in the compounds described herein (e.g., Formula I, Ia', Ia, II, III, IV, V, VI, VII, VIII, IX, X, XI, or XII and those in the seventeenth to nineteenth embodiment) is 1R,2S and the compounds are single enantiomers having an enantiomeric purity of at least 95% (e.g., at least 96%, at least 97%, at least 98%, at least 99%, at least 99.5%, or at least 99.9%).

In a twenty-third embodiment, the stereochemical configuration about the cyclopropyl ring in the compounds described herein (e.g., Formula I, Ia', Ia, II, III, IV, V, VI, VII, VIII, IX, X, XI, or XII and those in the seventeenth to nineteenth embodiment) is 1S,2R.

In a twenty-fourth embodiment, the stereochemical configuration about the cyclopropyl ring in the compounds described herein (e.g., Formula I, Ia', Ia, II, III, IV, V, VI, VII, VIII, IX, X, XI, or XII and those in the seventeenth to nineteenth embodiment) is 1S,2R and the compounds are single enantiomers having an enantiomeric purity of at least 95% (e.g., at least 96%, at least 97%, at least 98%, at least 99%, at least 99.5%, or at least 99.9%).

In one aspect, the compounds described herein are not

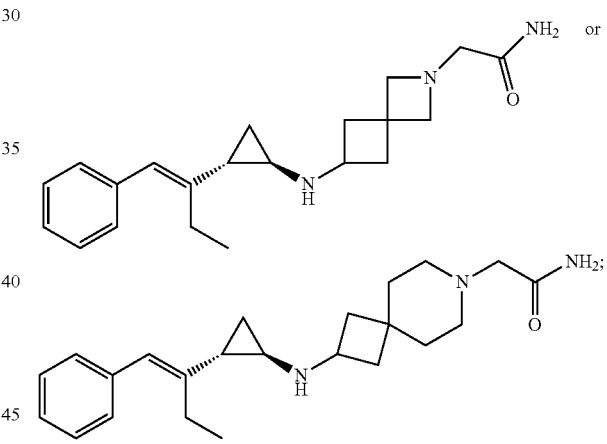

or a salt thereof.

In one aspect, when q is 0, m is 1, n is 1, o is 0, and $R^1$ and $R^2$ are both hydrogen in the compounds described herein then $R^5$ is not —$CONH_2$. In another aspect, when q is 0, m is 2, n is 2, o is 0, and $R^1$ and $R^2$ are both hydrogen in the compounds described herein then $R^5$ is not —$CONH_2$.

Specific examples of compounds are provided in the EXEMPLIFICATION section and are included as part of a fourteenth embodiment herein. Pharmaceutically acceptable salts as well as the neutral forms of the compounds in the EXEMPLIFICATION are also included.

4. Formulation and Administration

In one aspect, provided herein are compositions comprising the compounds described herein, or a pharmaceutically acceptable salt thereof.

In another aspect, the compositions further comprise a pharmaceutically acceptable carrier, adjuvant, or vehicle. The amount of compound in the composition is such that is effective to measurably modulate LSD1, or a mutant thereof in a biological sample or in a patient, i.e., the "effective amount" or "therapeutically effective amount."

In certain aspects, a composition described herein is formulated for administration to a patient in need of such composition. In some aspects, a composition described herein is formulated for oral administration to a patient.

The term "pharmaceutically acceptable carrier, adjuvant, or vehicle" or ""pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable compositions described herein may he orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Pharmaceutically acceptable compositions described herein may also be prepared in injectable form. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Pharmaceutically acceptable compositions described herein may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

The amount of a compound described herein that may be combined with the carrier materials to produce a composition in a single dosage form will vary depending upon the host treated and the particular mode of administration. In some embodiments, provided compositions should be formulated so that a dosage of between 0.01-100 mg/kg body weight/day of the inhibitor, such as e.g., 0.1-100 mg/kg body weight/day, can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of compound described herein in the composition will also depend upon the particular compound in the composition.

5. Uses of Compounds and Pharmaceutically Acceptable Compositions

In some embodiments, the compounds and compositions described herein are useful in treating diseases and/or disorders associated with overexpression of LSD1 and/or expression of a mutant form of LSD1, such as those mutant forms that alter LSD1 substrate activity.

In some embodiments, the compounds and compositions described herein are useful in treating diseases and/or disorders associated with cellular proliferation. In some embodiments, the compounds and compositions described herein are useful in treating diseases and/or disorders associated with misregulation of cell cycle or DNA repair. In some embodiments, the compounds and compositions described herein are useful in treating cancer. Exemplary types of cancer include breast cancer, prostate cancer, colon cancer, renal cell carcinoma, glioblastoma multiforme cancer, bladder cancer, melanoma, bronchial cancer, lymphoma and liver cancer.

In some embodiments, the present disclosure provides a method of reducing the activity of LSD1 in a subject comprising the step of administering a compound described herein, or a composition comprising any of the compounds herein. In some embodiments, the present disclosure provides a method of reducing the activity of widetype-LSD1 in a subject comprising the step of administering a compound described herein, or a composition comprising any of the foregoing. In some embodiments, the present disclosure provides a method of reducing the activity of a mutant form of LSD1 in a subject comprising the step of administering a compound described herein, or a composition comprising any of the foregoing.

In some embodiments, the present disclosure provides a method of treating a disease or condition related to cancer including e.g., tumors such as skin, breast, brain, cervical carcinomas, testicular carcinomas, etc. In one aspect, cancers that may be treated by the compositions and methods described herein include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas.

In some embodiments, the present disclosure provides a method of treating a disease or condition selected from one or more of the following, Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

In one embodiment, the present disclosure provides a method of treating a disease or condition seleted from CML, T-ALL, neuroblastoma, breast cancer, prostate cancer, herpes simplex virus reactivation, and HIV infection comprising the step of administering to a subject in need thereof a compound described herein, or a pharmaceutically acceptable salt thereof. In one alternative, the disease or condition is selected from CML, T-ALL, and neuroblastoma.

EXEMPLIFICATION

The representative examples that follow are intended to help illustrate the present disclosure, and are not intended to, nor should they be construed to, limit the scope of what is described. Modifications and further embodiments, in addition to those shown and described herein, will become apparent to those skilled in the art.

It will further be appreciated that the present disclosure (including the Exemplification) contemplates individual the compounds described herein. Where individual compounds exemplified are isolated and/or characterized as a salt, for example, as a trifluoroacetic acid salt, the present disclosure contemplates a free base of the salt, as well as other pharmaceutically acceptable salts of the free base.

Unless otherwise noted, all solvents, chemicals, and reagents were obtained commercially and used without purification. The $^1$H NMR spectra were obtained in $D_2O$, $CDCl_3$, $d_6$-DMSO, $CD_3OD$, or $d_6$-acetone at 25° C. at 400 MHz on an OXFORD (Varian) with chemical shift (δ, ppm) reported relative to TMS as an internal standard. HPLC-MS chromatograms and spectra were obtained with Shimadzu LC-MS-2020 system. Chiral analysis and purification were obtained with Yilite P270.

(1R,2S)-2-((E)-1-phenylbut-1-en-2-yl)cyclopropan-1-amine (S)-2-hydroxy-2-phenylacetate Step 1:

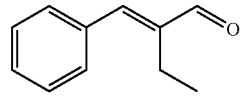

(E)-2-benzylidenebutanal

To a solution of benzaldehyde (130.0 kg, 1226.4 mol) in MeOH (1100.0 kg) was added NaOH (aq.) (10%, 500.0 kg). Then butanal (92.7 kg, 1287.5 mol) was added dropwise at 0° C. The reaction mixture was stirred at 10° C. for 10 h. The solvent was removed and the residue was acidified by HCl (aq., 4N) to pH=5. The mixture was extracted with EtOAc (500 kg+200 kg) and washed with brine (100 kg*2). The organic layer was concentrated under vacuum. The crude product was distilled under vacuum (85~95° C., 2-10 mmhg) to afford (E)-2-benzylidenebutanal (130.0 kg, GC>95%) as a yellowish oil.

Step 2:

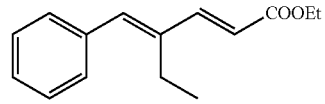 [SMILES: CCOC(=O)/C=C/C(=C/c1ccccc1)CC]

ethyl (E)-4-((E)-benzylidene)hex-2-enoate

Ethyl 2-(diethoxyphosphoryl)acetate (182.0 kg, 812.5 mol) was dissolved in THF (2200 kg) and cooled to 0° C. Potassium tert-butanolate (105.0 kg, 937.5 mol) was added in one portion and the reaction mixture was stirred vigorously at 0° C. for 15 min. (E)-2-benzylidenebutanal (130.0 kg, 812.5 mol 1.0 eq) was added to the reaction mixture and the reaction mixture was stirred at 25° C. for 16 h. The reaction mixture was quenched with $H_2O$ (320.0 kg) and extracted with EtOAc (360.0 kg). The organic layer was dried over sodium sulfate and filtered. The solvent was evaporated under reduced pressure to afford crude product as an oil. The oil was dissolved in petroleum ether (560.0 kg), filtered through a pad of silica gel (30.0 kg), and the filter cake was washed with petroleum ether. The combined filtrate was concentrated afford ethyl (E)-4-((E)-benzylidene)hex-2-enoate as an oil (170.0 kg). This material was used in the next step without further purification.

Step 3:

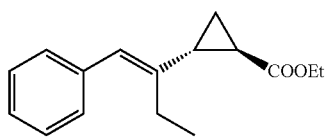 [SMILES: CCOC(=O)[C@@H]1C[C@H]1/C(=C/c1ccccc1)CC]

ethyl (trans)-2-((E)-1-phenylbut-1-en-2-yl)cyclopropane-1-carboxylate

Potassium tert-butanolate (103.5 kg, 924.1 mol) was dissolved in DMSO (1900 kg) under an inert atmosphere. The mixture was stirred for 15 min at 25° C. before addition of trimethylsulfoxonium iodide (210.0 kg, 959.0 mol). This mixture was stirred for 45 min at 25° C. before addition of ethyl (E)-4-((E)-benzylidene)hex-2-enoate (170.0 kg, 738.0 mol). The reaction was warmed to 50~55° C. and stirred for 16 h. The reaction was quenched with water (600 kg). The mixture was extracted with petroleum ether (800 kg). The petroleum ether phase was evaporated under reduced pressure to afford ethyl (trans)-2-((E)-1-phenylbut-1-en-2-yl)cyclopropane-1-carboxylate (76.5 kg) as brown liquid. This material was used in the next step without further purification Step 4:

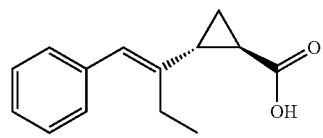 [SMILES: CC/C(=C\c1ccccc1)[C@@H]1C[C@H]1C(=O)O]

(trans)-2-(((E)-1-phenylbut-1-en-2-yl)cyclopropane-1-carboxylic acid

Ethyl (trans)-2-((E)-1-phenylbut-1-en-2-yl)cyclopropane-1-carboxylate (76.5 kg kg, 313.1 mol) was dissolved in water (320 kg) and methanol (360 kg). To this solution was added sodium hydroxide (41.0 kg, 1025 mol) and the solution was stirred for 3 h at 50° C. The mixture was concentrated to about 300 L and acidified to pH=4 using HCl (aq., 4N). This solution was extracted with EtOAc (520 kg) and the layers separated. The organic layer was washed with brine, dried over sodium sulfate, filtered, and concentrated to afford (trans)-2-((E)-1-phenylbut-1-en-2-yl)cyclopropane-1-carboxylic acid (62.5 kg). This material was used in next step without further purification.

Step 5:

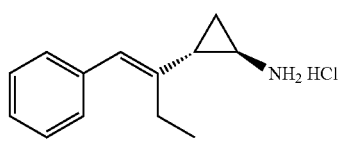

(trans)-2-((E)-1-phenylbut-1-en-2-yl)cyclopropan-1-amine hydrochloride

To a solution of (trans)-2-((E)-1-phenylbut-1-en-2-yl)cyclopropane-1-carboxylic acid (26.0 kg, 120.4 mol) in toluene (270 kg) were added triethylamine (36.3 kg, 359 mol) and diphenylphosphoryl azide (38.0 kg, 138.1 mol) at 0° C. The reaction mixture was stirred at 0~10° C. for 3 h. Water (100 kg) was added and the mixture was extracted with EtOAc (80.0 kg) and the organic layer was concentrated under vacuum to afford a crude oil. The crude oil was dissolved in petroleum ether (50 kg). The suspension was filtered through a pad of silica gel and the filter cake was washed with petroleum ether. The combined filtrates were concentrated to afford crude acyl azide. The crude acyl azide was taken up in toluene (100 kg) and the solution was heated to 85° C. for 2 h. The organic layer was concentrated to ~60 L. Potassium trimethylsilanolate (23.0 kg, 177.9 mol) was added to the toluene mixture at room temperature and stirred for 1.5 h. The reaction was then treated with HCl (2N aq., 120 kg) and stirred. The layers were separated. The organic layer was extracted twice with HCl (2N aq., 20 kg) and the aqueous extracts were combined. The aqueous layer was extracted with MTBE (30 kg) once, and then basified to pH=10-11 with sodium hydroxide (47 kg, 30% aqueous). The aqueous layer was then extracted with MTBE (150 kg). The organic extracts were washed with brine, dried with sodium sulfate and filtered. To this MTBE solution was added HCl (23.5 kg, 12% in diethyl ether) and a white solid precipitated from solution. The solid was collected to afford (trans)-2-((E)-1-phenylbut-1-en-2-yl)cyclopropan-1-amine hydrochloride (16.5 kg, 73.8 mol).

Step 6:

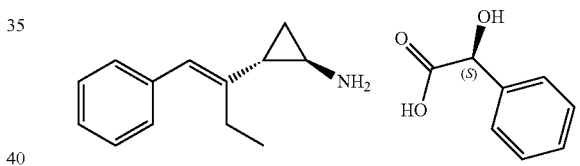

(1R,2S)-2-((E)-1-phenylbut-1-en-2-yl)cyclopropan-1-amine (S)-2-hydroxy-2-phenylacetate (trans)-2-((E)-1-phenylbut-1-en-2-yl)cyclopropan-1-amine hydrochloride (16.5 kg, 73.8 mol) was charged to a reactor and K₃PO₄ (46 L, 37 wt %) was added followed by EtOAc (150 kg). The reaction mixture was stirred at 0~10° C. for 3 h. The organic layer was separated and concentrated to dryness to afford an oil. S-Mandelic acid (8.4 kg, 55.35 mol) and 95% EtOH (165 kg) were added to the reactor and the reaction was stirred at room temperature for 72 h (until ee>99%). The solid was collected via filtration to afford (1R,2S)-2-((E)-1-phenylbut-1-en-2-yl)cyclopropan-1-amine (S)-2-hydroxy-2-phenylacetate (5.8 kg, 17.1 mol). LCMS m/z 188 [M+H]⁺. The absolute stereochemistry was determined by X-ray crystallography. See FIG. 1.

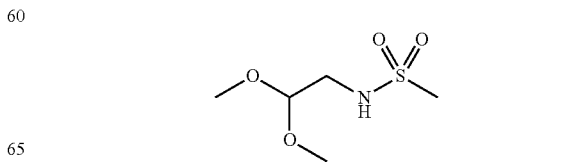

N-(2,2-dimethoxyethyl)methanesulfonamide

To a solution of 2,2-dimethoxyethanamine (518 μL, 4.75 mmol) in dichloromethane (4.75 mL) at 0° C. was added triethylamine (1.32 mL, 9.50 mmol) followed by methanesulfonyl chloride (550 μL, 7.12 mmol). The mixture was stirred at 0° C. for 30 minutes. The reaction was diluted with dichloromethane and washed with saturated aqueous sodium bicarbonate. The aqueous layer was extracted twice with dichloromethane. The combined organic layers were dried with sodium sulfate then concentrated under reduced pressure to afford 1.18 g of crude compound as light yellow oil. The crude mixture was then diluted in acetone:water (1:1, 4 mL) and treated with amberlyst-15 hydrogen form (1.2 g). The resulting mixture was stirred for 2 hours at room temperature. The suspension was filtered through celite and concentrated under reduced pressure to afford crude N-(2,2-dimethoxyethyl)methanesulfonamide (900 mg) as a yellow oil. The product was used without further purification. $^1$H NMR (400 MHz, dmso) δ 7.13 (t, J=6.0 Hz, 1H), 4.36 (t, J=5.5 Hz, 1H), 3.28 (s, 6H), 3.02 (t, J=5.7 Hz, 2H), 2.90 (s, 3H).

N-(2-oxoethyl)ethanesulfonamide

Step 1:

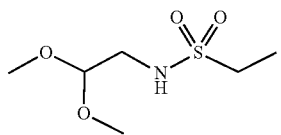

N-(2,2-dimethoxyethyl)ethanesulfonamide

To a solution of 2,2-dimethoxyethanamine (247 μL, 2.28 mmol) in DCM (1.9 mL) at 0° C. was added triethylamine (634 μL, 4.56 mmol) followed by ethanesulfonyl chloride (212 μL, 2.28 mmol). The mixture was stirred at 0° C. for 30 min. The reaction was diluted with DCM and washed with sat. NaHCO$_3$. The aqueous layer was back-extracted twice with DCM. The combined organic layers were dried with Na$_2$SO$_4$ and then concentrated under reduced pressure to afford crude N-(2,2-dimethoxyethyl)ethanesulfonamide as a brown oil.

Step 2:

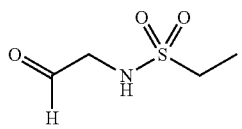

N-(2-oxoethyl)ethanesulfonamide

To a solution of crude N-(2,2-dimethoxyethyl)ethanesulfonamide in acetone: water (1:1, 4 mL) was added Amberlyst-15 Hydrogen form (1.0 g). The resulting mixture was stirred over two days at room temperature. The suspension was filtered through celite and concentrated under reduced pressure to afford crude N-(2-oxoethyl)ethanesulfonamide (614 mg) as a yellow oil. Used without further purification. 1H NMR (400 MHz, CDCl$_3$) δ 9.68 (s, J=1.1 Hz, 1H), 4.15 (d, J=5.2 Hz, 2H), 3.07 (q, J=7.4 Hz, 2H), 1.40 (t, J=7.4 Hz, 3H).

Using the appropriate starting material and modifications the following intermediates in Table 1 were synthesized using the synthetic procedures described for N-(2-oxoethyl)ethanesulfonamide.

TABLE 1

| Structure | Name |
|---|---|
| 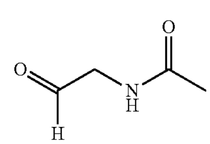 | N-(2-oxoethyl)acetamide |
| 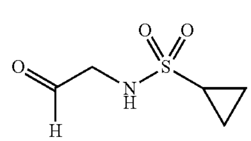 | N-(2-oxoethyl)cyclopropanesulfonamide |
| 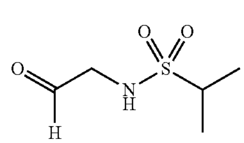 | N-(2-oxoethyl)propane-2-sulfonamide |
| 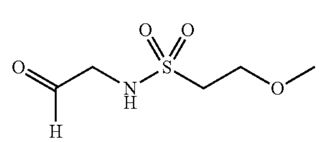 | 2-methoxy-N-(2-oxoethyl)ethane-1-sulfonamide |

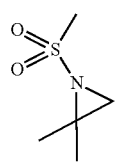

2,2-dimethyl-1-(methylsulfonyl)aziridine

To a solution of 2-amino-2-methylpropan-1-ol (1.0 g, 11.2 mmol) in DCM (22.4 mL) at 0° C. was added triethylamine (7.79 mL, 56.0 mmol) followed by methanesulfonyl chloride (2.16 mL, 28.0 mmol). The mixture was stirred at 0° C. for 30 min and was then allowed to warm to room temperature overnight. The reaction was diluted with DCM and washed with sat. NaHCO$_3$. The aqueous layer was extracted once with DCM. The combined organic layers were dried over Na$_2$SO$_4$ and then concentrated under reduced pressure to afford crude 2,2-dimethyl-1-(methylsulfonyl)aziridine (1.95 g) compound as a brown oil.

2,2,2-trifluoro-N-((1R,2S)-2-(E)-1-phenylbut-1-en-2-yl)cyclopropyl)-N-(7-azaspiro[3.5]nonan-2-yl)acetamide hydrochloride Step 1:

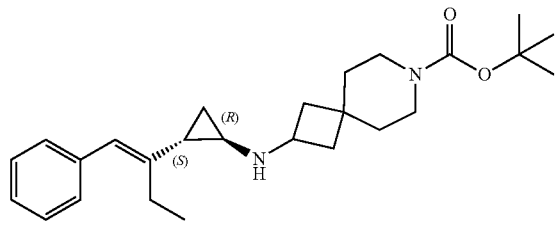

tert-butyl 2-(((1R,2S)-2-((E)-1-phenylbut-1-en-2-yl)cyclopropyl)amino)-7-azaspiro[3.5]nonane-7-carboxylate To a suspension of (1R,2S)-2-((E)-1-phenylbut-1-en-2-yl)cyclopropanamine (S)-2-hydroxy-2-phenylacetate (3.5 g, 10.3 mmol) in 1,2-dichloroethane (75 mL) at 0° C. was added tert-butyl 2-oxo-7-azaspiro[3.5]nonane-7-carboxylate (2.58 g, 10.8 mmol) followed by sodium triacetoxyborohydride (4.78 g, 22.6 mmol). The reaction mixture was allowed to warm to 23° C. and stirred for 4 hours. Additional tert-butyl 2-oxo-7-azaspiro[3.5]nonane-7-carboxylate (123 mg, 0.51 mmol) and sodium triacetoxyborohydride (328 mg, 1.55 mmol) were then added and the reaction mixture was stirred at 23° C. for 2 hours. The reaction mixture was then diluted with a saturated aqueous K$_2$CO$_3$ solution (50 mL) and extracted with DCM (3×20 mL). The combined organic layers were washed with brine (20 mL), dried over Na$_2$SO$_4$, filtered, and concentrated under reduced pressure. The crude residue was purified via Biotage (gradient 0 to 100% EtOAc in hexanes) to afford tert-butyl 2-(((1R,2S)-2-((E)-1-phenylbut-1-en-2-yl)cyclopropyl)amino)-7-azaspiro[3.5]nonane-7-carboxylate (3.235 g). LCMS (ESI) m/z 411.3 [M+H]$^+$.

Step 2:

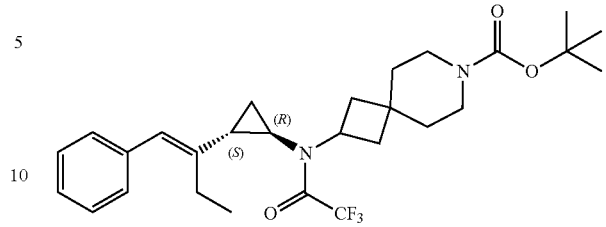

tert-butyl 2-(2,2,2-trifluoro-N-((1R,2S)-2-((E)-1-phenylbut-1-en-2-yl)cyclopropyl)acetamido)-7-azaspiro[3.5]nonane-7-carboxylate To a solution of tert-butyl 2-(((1R,2S)-2-((E)-1-phenylbut-1-en-2-yl)cyclopropyl)amino)-7-azaspiro[3.5]nonane-7-carboxylate (3.226 g, 7.84 mmol) in DCM (50 mL) at 0° C. was added N,N-diisopropylethylamine (2.03 mL, 11.7 mmol) followed by trifluoroacetic anhydride (1.40 mL, 10.1 mmol). The reaction mixture was allowed to warm to 23° C. and stirred for 4 hours. The reaction mixture was then diluted with a saturated aqueous NaHCO$_3$ solution (30 mL) and the two layers were separated. The organic layer was washed with a saturated aqueous NH$_4$Cl solution (2×20 mL), dried over Na$_2$SO$_4$, filtered, and concentrated under reduced pressure. The crude residue was purified via Biotage (gradient 0 to 50% EtOAc in hexanes) to afford tert-butyl 2-(2,2,2-trifluoro-N-((1R,2S)-2-((E)-1-phenylbut-1-en-2-yl)cyclopropyl)acetamido)-7-azaspiro[3.5]nonane-7-carboxylate (3.258 g). LCMS (ESI) m/z: 529.2 [M+Na]$^+$.

Step 3:

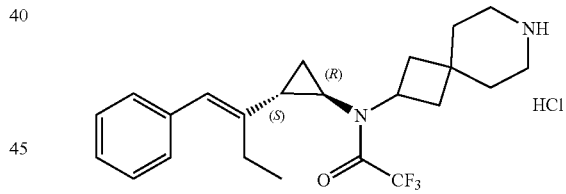

2,2,2-trifluoro-N-((1R,2S)-2-((E)-1-phenylbut-1-en-2-yl)cyclopropyl)-N-(7-azaspiro[3.5]nonan-2-yl)acetamide hydrochloride To a solution of tert-butyl 2-(2,2,2-trifluoro-N-((1R,2S)-2-((E)-1-phenylbut-1-en-2-yl)cyclopropyl)acetamido)-7-azaspiro[3.5]nonane-7-carboxylate (3.254 g, 6.41 mmol) in dioxane (32 mL) at 23° C. was added a 4.0 M solution of HCl in dioxane (12.8 mL, 51.2 mmol) dropwise. The reaction mixture was stirred at 23° C. for 2 hours. Additional HCl (12.8 mL, 51.2 mmol, 4.0 M solution in dioxane) was then added and the reaction mixture was stirred at 23° C. for 2 hours. The reaction mixture was then concentrated under reduced pressure to afford 2,2,2-trifluoro-N-((1R,2S)-2-((E)-1-phenylbut-1-en-2-yl)cyclopropyl)-N-(7-azaspiro[3.5]nonan-2-yl)acetamide hydrochloride as a crude yellow foam (3.185 g). LCMS (ESI) m/z: 407.2 [M+H]$^+$.

2,2,2-trifluoro-N-((1R, 2S)-2-((E)-1-phenylbut-1-en-2-yl)cyclopropyl)-N-(2-azaspiro[3.3]heptan-6-yl)acetamide 2,2,2-trifluoroacetate Step 1:

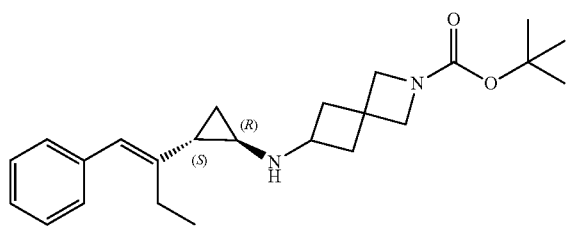

tert-butyl 6-(((1R,2S)-2-((E)-1-phenylbut-1-en-2-yl)cyclopropyl)amino)-2-azaspiro[3.3]heptane-2-carboxylate To (1R,2S)-2-((E)-1-phenylbut-1-en-2-yl)cyclopropanamine (S)-2-hydroxy-2-phenylacetate (8.65 g, 25.5 mmol) and tert-butyl 6-oxo-2-azaspiro[3.3]heptane-2-carboxylate (5.15 g, 24.3 mmol) in 1,2-DCE (100 mL) was added sodium triacetoxyborohydride (10.8 g, 51 mmol). After 30 min. the reaction was quenched with K$_2$CO$_3$ (aq.) and extracted with DCM (2×150 mL). The organic phase was concentrated and the crude residue was purified via column chromatography (50 g column, 5% to 100% EtOAc:hexanes) to afford tert-butyl 6-(((1R,2S)-2-((E)-1-phenylbut-1-en-2-yl)cyclopropyl)amino)-2-azaspiro[3.3]heptane-2-carboxylate (4.61 g). LCMS m/z: 383.7 [M+H]$^+$.

Step 2:

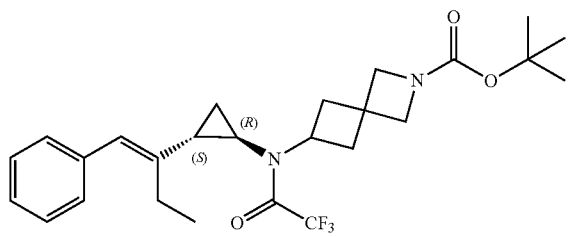

tert-butyl 6-(2,2,2-trifluoro-N-((1R,2S)-2-((E)-1-phenylbut-1-en-2-yl)cyclopropyl)acetamido)-2-azaspiro[3.3]heptane-2-carboxylate To tert-butyl 6-(((1R,2S)-2-((E)-1-phenylbut-1-en-2-yl)cyclopropyl)amino)-2-azaspiro[3.3]heptane-2-carboxylate (4.61 g, 12 mmol) dissolved in DCM was added diisopropylethylamine (2.81 mL, 16.2 mmol). The solution was cooled to 0° C. before addition of trifluoroacetic anhydride (2.08 mL, 15 mmol). The reaction mixture was stirred for 2 h, while warming to room temperature. The volatiles were evaporated under reduced pressure to afford crude tert-butyl 6-(2,2,2-trifluoro-N-((1R,2S)-2-((E)-1-phenylbut-1-en-2-yl)cyclopropyl)acetamido)-2-azaspiro[3.3]heptane-2-carboxylate. LCMS m/z 479 [M+H]$^+$.

Step 3:

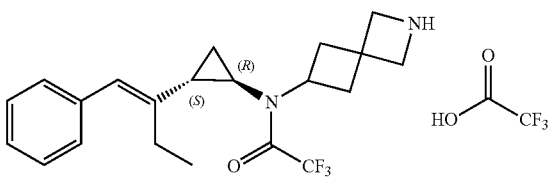

2,2,2-trifluoro-N-((1R,2S)-2-((E)-1-phenylbut-1-en-2-yl)cyclopropyl)-N-(2-azaspiro[3.3]heptan-6-yl)acetamide 2,2,2-trifluoroacetate Tert-butyl 6-(2,2,2-trifluoro-N-((1R, 2S)-2-((E)-1-phenylbut-1-en-2-yl)cyclopropyl)acetamido)-2-azaspiro[3.3]heptane-2-carboxylate (5.74 g, 12 mmol) was dissolved in DCM (80 mL) and cooled to 10° C. before addition of trifluoroacetic acid (20 mL, 240 mmol). The solution was allowed to warm to room temperature and stirred for 3 h. The reaction was concentrated to afford crude 2,2,2-trifluoro-N-((1R,2S)-2-((E)-1-phenylbut-1-en-2-yl)cyclopropyl)-N-(2-azaspiro[3.3]heptan-6-yl)acetamide 2,2,2-trifluoroacetate. LCMS m/z 379.2 [M+H]$^+$.

Compound 1: 2-(6-(((1R,2S)-2-((E)-1-phenylbut-1-en-2-yl)cyclopropyl)amino)-2-azaspiro[3.3]heptan-2-yl)ethanol Step 1:

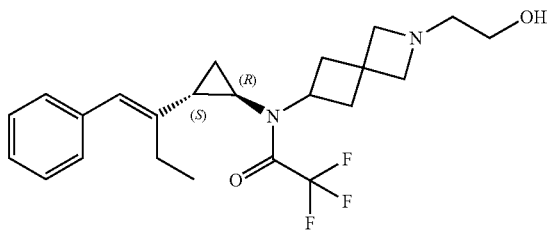

2,2,2-trifluoro-N-(2-(2-hydroxyethyl)-2-azaspiro[3.3]heptan-6-yl)-N-((1R,2S)-2-((E)-1-phenylbut-1-en-2-yl)cyclopropyl)acetamide A solution of 2,2,2-trifluoro-N-((1R,2S)-2-((E)-1-phenylbut-1-en-2-yl)cyclopropyl)-N-(2-azaspiro[3.3]heptan-6-yl)acetamide 2,2,2-trifluoroacetate (7.57 g, 15.3 mmol) and glycoaldehyde dimer (5.51 g, 45.9 mmol) in methanol was treated with acetic acid (2.0 mL) and sodium cyanoborohydride (2.88 g, 45.9 mmol). The reaction was heated to 60° C. and monitored by LCMS. After 1 hour, the reaction was quenched with 10% aqueous potassium carbonate to a pH of 8. Volatiles were then removed under vacuum. The crude mixture was extracted twice with 2-methyltetrahydrofuran. The organic layer was then dried with sodium sulfate, filtered and volatiles were removed under vacuum. The desired product 2,2,2-trifluoro-N-(2-(2-hydroxyethyl)-2-azaspiro[3.3]heptan-6-yl)-N-((1R,2S)-2-((E)-1-phenylbut-1-en-2-yl)cyclopropyl)acetamide was used without further purification. LCMS (ESI) m/z: 423.1 [M+H]$^+$.

Step 2:

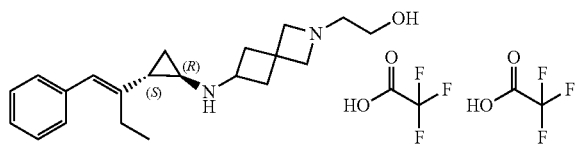

2-(6-(((1R,2S)-2-((E)-1-phenylbut-1-en-2-yl)cyclopropyl)amino)-2-azaspiro[3.3]heptan-2-yl)ethanol bis(2,2,2-trifluoroacetate)

To a round bottom flask, 2,2,2-trifluoro-N-(2-(2-hydroxyethyl)-2-azaspiro[3.3]heptan-6-yl)-N-((1R,2S)-2-((E)-1-phenylbut-1-en-2-yl)cyclopropyl)acetamide (6.46 g, 15.3 mmol) was dissolved in methanol (75 mL), cooled to 0° C. and treated with 10 mL of 10% aqueous sodium hydroxide. The reaction was stirred under nitrogen atmosphere for 30 minutes and was quenched with 2,2,2-trifluoroacetic acid to a pH of 2.0. Volatiles were removed under vacuum. The desired product was purified by reverse phase column chromatography using 10-30% CH$_3$CN/0.1% aqueous 2,2,2-trifluoroacetic acid. Pure fractions were combined, frozen and lyophilized to afford 2-(6-(((1R,2S)-2-((E)-1-phenylbut-1-en-2-yl)cyclopropyl)amino)-2-azaspiro[3.3]heptan-2-yl)ethanol bis-(2,2,2-trifluoroacetic acid) (2.90 g). LCMS (ESI) m/z: 327.3 [M+H]$^+$. $^1$H NMR (400 MHz, DMSO-d$_6$) δ 9.87 (br s, 1H), 9.21 (br s, 2H), 7.39-7.31 (m, 2H), 7.27-7.17 (m, 3H), 6.21 (s, 1H), 5.23 (br s, 1H), 4.25-4.11 (m, 2H), 4.11-4.06 (m, 1H), 3.98 (m, 1H), 3.85-3.69 (m, 1H), 3.55 (s, 2H), 3.25-3.11 (m, 2H), 2.80-2.72 (m, 1H), 2.72-2.65 (m, 1H), 2.65-2.53 (m, 1H), 2.48 -2.35 (m, 2H), 2.30-21.8 (m, 2H), 2.02-1.90 (m, 1H), 1.22-1.14 (m, 2H), 1.12 (t, J=7.6 Hz, 3H).

Compound 2: 2-(6-(((1R,2S)-2-((E)-1-phenylbut-1-en-2-yl)cyclopropyl)amino)-2-azaspiro[3.3]heptan-2-yl)propane-1,3-diol Step 1:

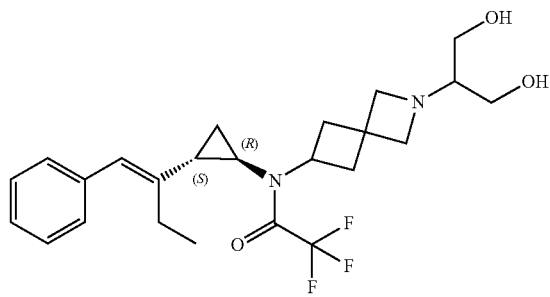

N-(2-(1,3-dihydroxypropan-2-yl)-2-azaspiro[3.3]heptan-6-yl)-2,2,2-trifluoro-N-((1R,2S)-2-((E)-1-phenylbut-1-en-2-yl)cyclopropyl)acetamide To a round bottom flask, 2,2,2-trifluoro-N-((1R,2S)-2-((E)-1-phenylbut-1-en-2-yl)cyclopropyl)-N-(2-azaspiro[3.3]heptan-6-yl)acetamide 2,2,2-trifluoroacetate (2.75 g, 5.58 mmol) dissolved in methanol (18.6 mL) was added 1,3-dihydroxypropan-2-one (3.0 g, 33.4 mmol) and acetic acid (10 drops). The solution was then treated with sodium cyanoborohydride (2.09 g, 33.4 mmol) and stirred for 1 h. The reaction was then quenched to pH 8 using 10% potassium carbonate aqueous and volatiles were removed under vacuum. The crude mixture was extracted twice with 2-methyltetrahydrofuran. The combined organic layers were washed once with brine, then dried with sodium sulfate, filtered and concentrated to afford crude N-(2-(1,3-dihydroxypropan-2-yl)-2-azaspiro[3.3]heptan-6-yl)-2,2,2-trifluoro-N-((1R,2S)-2-((E)-1-phenylbut-1-en-2-yl)cyclopropyl)acetamide. The crude product was used without further purification. LCMS (ESI) m/z: 453.4 [M+H]$^+$.

Step 2:

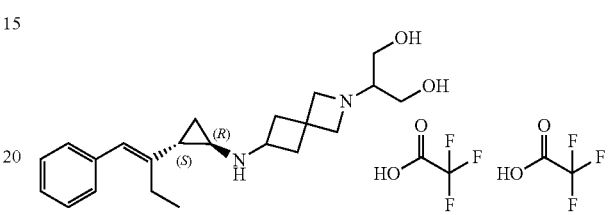

2-(6-(((1R,2S)-2-((E)-1-phenylbut-1-en-2-yl)cyclopropyl)amino)-2-azaspiro[3.3]heptan-2-yl)propane-1,3-diol bis(2,2,2-trifluoroacetate)

N-(2-(1,3-dihydroxypropan-2-yl)-2-azaspiro[3.3]heptan-6-yl)-2,2,2-trifluoro-N-((1R,2S)-2-((E)-1-phenylbut-1-en-2-yl)cyclopropyl)acetamide (2.52 g, 5.58 mmol) was dissolved in methanol, cooled in an ice bath and treated with 10% aqueous NaOH and allowed to reach room temperature. After 30 min, the reaction was quenched to pH 2 using TFA, and volatiles were removed under reduced pressure. The crude mixture was purified by reverse phase column chromatography (60 g) using 10-30% MeCN/0.1% TFA aq. as eluent. Fractions were combined, frozen and lyophilized to afford 2-(6-(((1R,2S)-2-((E)-1-phenylbut-1-en-2-yl)cyclopropyl)amino)-2-azaspiro[3.3]heptan-2-yl)propane-1,3-diol bis(2,2,2-trifluoroacetate) as a white amorphous solid (740 mg). LCMS (ESI) m/z: 357.4 [M+H]$^+$. $^1$H NMR (400 MHz, DMSO-d$_6$) δ 10.00 (s br, 1H), 9.33 (s br, 2H), 7.42-7.31 (m, 2H), 7.28-7.16 (m, 3H), 6.20 (s, 1H), 5.28 (s br, 2H), 4.30 (t, J=15.6 Hz, 2H), 4.14 (s, 1H), 3.99 (s, 1H), 3.86-3.68 (m, 1H), 3.58 (dd, J=12.7, 9.6 Hz, 4H), 3.29 (s, 2H), 2.72 (s, 2H), 2.40 (d, J=8.6 Hz, 1H), 2.31-2.15 (m, 2H), 1.97 (s, 1H), 1.15 (dt, J=15.1, 5.9 Hz, 5H).

Scale Up and Formation of Monocitrate Salt of 2-(6-(((1R,2S)-2-((E)-1-phenylbut-1-en-2-yl)cyclopropyl)amino)-2-azaspiro[3.3]heptan-2-yl)propane-1,3-diol Step 1:

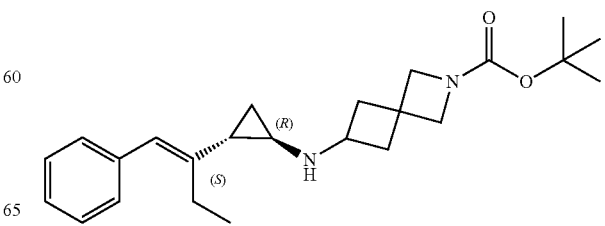

tert-butyl 6-(((1R,2S)-2-((E)-1-phenylbut-1-en-2-yl)cyclopropyl)amino)-2-azaspiro[3.3]heptane-2-carboxylate Charge (1R,2S)-2-((E)-1-phenylbut-1-en-2-yl)cyclopropan-1-amine (S)-2-hydroxy-2-phenylacetate (160 g, 1.0 eq.) into a 3 L flask and dissolved in DCM (1000 mL). To this flask was added a solution of 10% $K_2CO_3$ (500 mL) and water (500 mL). The solution was stirred for 10 min. The layers were separated and the aqueous layer was extracted with DCM (2×, 300 mL). The combined organics layer was dried over $Na_2SO_4$ (100 g), filtered, and concentrated to afford (1R,2S)-2-((E)-1-phenylbut-1-en-2-yl)cyclopropan-1-amine as a light yellow oil. This material was dissolved in 2-MeTHF (500 mL) and concentrated. This material was then dissolved in 2-MeTHF (1000 mL) and transferred to a 10 L flask. To the 10 L flask was added 2-MeTHF (1000 mL) to completely dissolved the freebase and to this solution was added tert-butyl 6-oxo-2-azaspiro[3.3]heptane-2-carboxylate (100 g). The reaction was stirred for 10 min before addition of $NaBH(OAc)_3$ (200 g, 2.0 eq). The reaction was stirred at room temperature for 4 h. Additional $NaBH(OAc)_3$ (8 g, 0.08 eq) was added and the solution was stirred at room temperature for 2 h. This solution was basified to pH=8 via addition of a 10% $K_2CO_3$ solution (950 mL) and the reaction was stirred for 30 min at room temperature. The layers were separated and the water layer was extracted with DCM (1×, 500 mL). The combined organics layer was concentrated (bath temperature<45° C.) to afford crude tert-butyl 6-(((1R,2S)-2-((E)-1-phenylbut-1-en-2-yl)cyclopropyl)amino)-2-azaspiro[3.3]heptane-2-carboxylate (220 g).

Step 2:

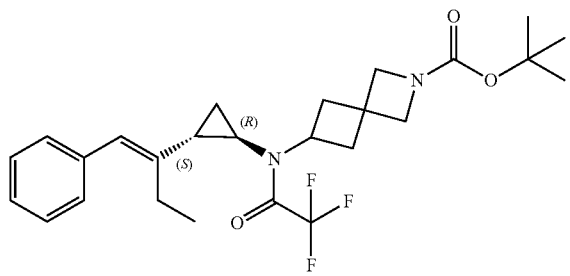

tert-butyl 6-(2,2,2-trifluoro-N-((1R,2S)-2-((E)-1-phenylbut-1-en-2-yl)cyclopropyl)acetamido)-2-azaspiro[3.3]heptane-2-carboxylate To a flask charged with crude tert-butyl 6-(((1R,2S)-2-((E)-1-phenylbut-1-en-2-yl)cyclopropyl)amino)-2-azaspiro[3.3]heptane-2-carboxylate (200 g) was added DCM (2000 mL) and Hunig's base (100 mL). The reaction was cooled to 0° C. before addition of trifluoroacetic anhydride (120 g) dropwise over 30 min. The reaction was stirred at 0° C. before warming to 10-20° C. and stirring for 16 h. Water (2000 mL) was added to this reaction and the layers were separated. The organics layer was concentrated to afford crude product (264 g). The crude oil was dissolved in heptane (500 mL) and stirred for 30 min to afford a suspension. This material was then purified via silica gel chromatography (1.5 kg, 100-200 mech silica gel; gradient: 1:20 ethyl acetate:heptane; 1:10 ethyl acetate heptane; 1:5 ethyl acetate:heptane) to obtain tert-butyl 6-(2,2,2-trifluoro-N-((1R,2S)-2-((E)-1-phenylbut-1-en-2-yl)cyclopropyl)acetamido)-2-azaspiro[3.3]heptane-2-carboxylate (Fraction A: 114 g, 96% pure; Fraction B: 72 g, 86% pure).

Step 3:

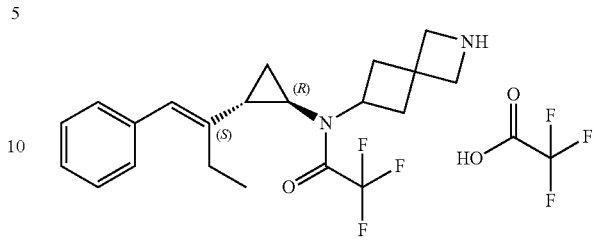

2,2,2-trifluoro-N-((1R,2S)-2-((E)-1-phenylbut-1-en-2-yl)cyclopropyl)-N-(2-azaspiro[3.3]heptan-6-yl)acetamide 2,2,2-trifluoroacetate To a flask charged with tert-butyl 6-(2,2,2-trifluoro-N-((1R,2S)-2-((E)-1-phenylbut-1-en-2-yl)cyclopropyl)acetamido)-2-azaspiro[3.3]heptane-2-carboxylate (104 g) was added DCM (1050 mL) and the solution was cooled to 0° C. To this solution was added TFA (240 g, 10 eq.) and the solution was warmed to room temperature. The reaction was stirred for 2 h before additional TFA (40 g, 2.0 eq.) was added. The reaction was stirred for 1 h before being concentrated to afford a brown oil. The brown oil was dissolved in MeOH (500 mL) and concentrated. This step was repeated (3×) to afford crude 2,2,2-trifluoro-N-((1R,2S)-2-((E)-1-phenylbut-1-en-2-yl)cyclopropyl)-N-(2-azaspiro[3.3]heptan-6-yl)acetamide 2,2,2-trifluoroacetate (365.7 g).

Step 4:

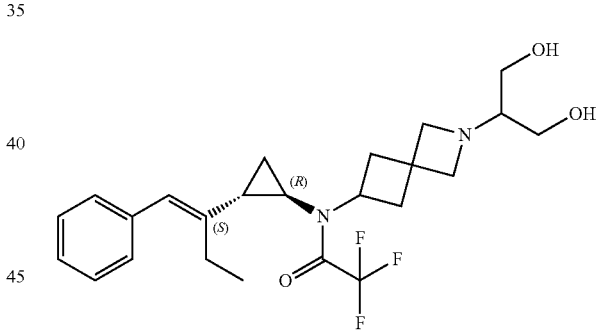

N-(2-(1,3-dihydroxypropan-2-yl)-2-azaspiro[3.3]heptan-6-yl)-2,2,2-trifluoro-N-((1R,2S)-2-((E)-1-phenylbut-1-en-2-yl)cyclopropyl)acetamide To a flask charged with crude 2,2,2-trifluoro-N-((1R,2S)-2-((E)-1-phenylbut-1-en-2-yl)cyclopropyl)-N-(2-azaspiro[3.3]heptan-6-yl)acetamide 2,2,2-trifluoroacetate (365.7 g, 1.0 eq.) was added MeOH (1500 mL). To this solution was added 1,3-dihydroxypropan-2-one (120 g, 1.33 eq.) and the solution was stirred a room temperature for 20 min before addition of AcOH (20 mL, 1.41 eq.). The reaction was stirred for 10 min before addition of $NaBH_3CN$ (84 g, 6.01 eq.). The reaction was placed in a cold bath to keep the temperature below 40° C. The reaction was stirred for 1 h and during the course of the reaction the mixture turned light yellow. This solution was basified to pH=8 via addition of 10% $K_2CO_3$ solution (400 mL). The mixture was concentrated to remove the MeOH (bath temperature<45° C.). The resulting solution was dissolved in DCM (500 mL) and water (200 mL) was added. The layers were separated and the aqueous layer was extracted with DCM (2×). The combined organics layers were dried over Na$_2$SO$_4$, filtered, and concentrated to afford crude N-(2-(1,3-dihydroxypropan-2-yl)-2-azaspiro[3.3]heptan-6-yl)-2,2,2-trifluoro-N-((1R,2S)-2-((E)-1-phenylbut-1-en-2-yl)cyclopropyl)acetamide (110.6 g).

Step 5:

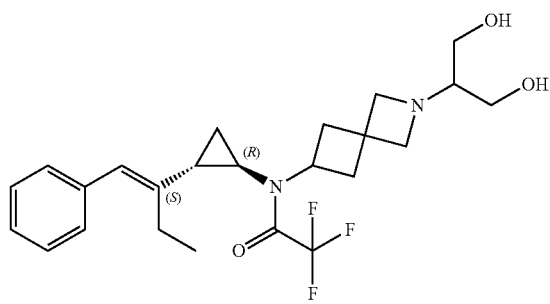

2-(6-(((1R,2S)-2-((E)-1-phenylbut-1-en-2-yl)cyclopropyl)amino)-2-azaspiro[3.3]heptan-2-yl)propane-1,3-diol To a flask charged with crude N-(2-(1,3-dihydroxypropan-2-yl)-2-azaspiro[3.3]heptan-6-yl)-2,2,2-trifluoro-N-((1R,2S)-2-((E)-1-phenylbut-1-en-2-yl)cyclopropyl)acetamide (110.6 g) was added 2-MeTHF (1100 mL). To this mixture was slowly added NaOH solution (20 g NaOH dissolved in 500 mL water). The reaction was stirred at room temperature for 1 h. The layers were separated and the aqueous layer was extracted with 2-MeTHF (2×). The combined organics layers were washed with brine, dried over Na$_2$SO$_4$, filtered, and concentrated to afford a yellow oil (190 g). The yellow oil was dissolved in ethyl acetate and washed with brine. The organics layer was concentrated (bath temperature<45° C.) to afford 2-(6-(((1R,2S)-2-((E)-1-phenylbut-1-en-2-yl)cyclopropyl)amino)-2-azaspiro[3.3]heptan-2-yl)propane-1,3-diol (76.4 g) as a light yellow solid.

Step 6:

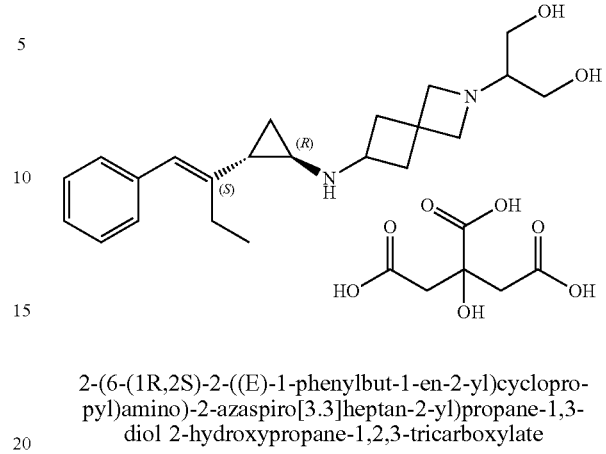

Figure 2:
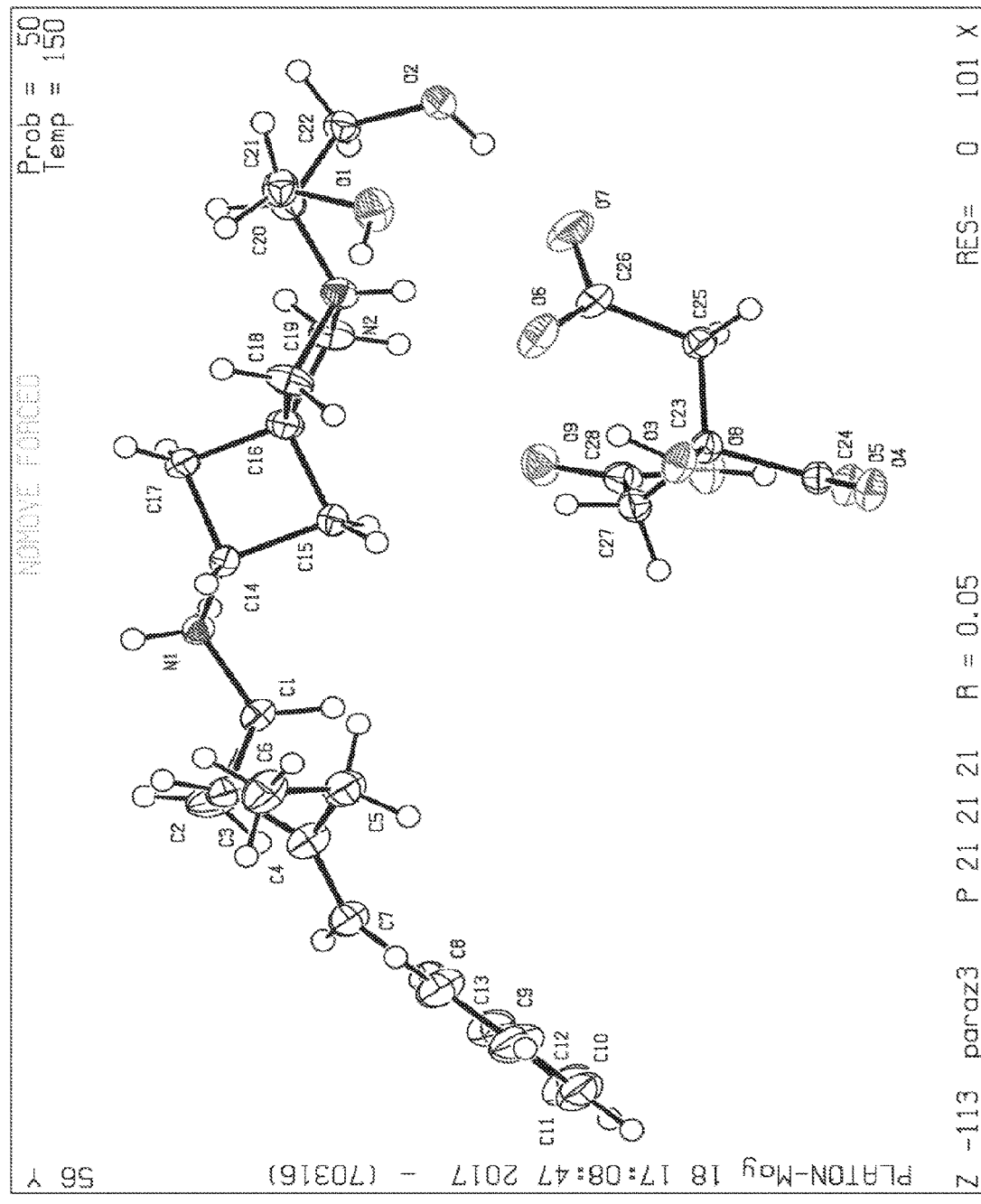
FIG. 2 depicts the X-ray crystal structure for the monocitrate salt of Compound 2.

2-(6-(1R,2S)-2-((E)-1-phenylbut-1-en-2-yl)cyclopropyl)amino)-2-azaspiro[3.3]heptan-2-yl)propane-1,3-diol 2-hydroxypropane-1,2,3-tricarboxylate To a flask charged with 2-((E)-1-phenylbut-1-en-2-yl)cyclopropyl)amino)-2-azaspiro[3.3]heptan-2-yl)propane-1,3-diol (50 g, 1.0 eq.) was added a mixture of DCM:MeOH (500 mL:40 mL). This solution was stirred at room temperature for 10 min before dropwise addition of citric acid (40 g, 1.43 eq) dissolved in MeOH (90 mL). The mixture was stirred at room temperature for 1 h before the precipitate was collected via filtration. The solid was washed with a mixture of MeOH:DCM (3:20, 200 mL). The filter cake was dried under vacuum at 40° C. for 16 h to afford 2-(6-(((1R,2S)-2-((E)-1-phenylbut-1-en-2-yl)cyclopropyl)amino)-2-azaspiro[3.3]heptan-2-yl)propane-1,3-diol 2-hydroxypropane-1,2,3-tricarboxylate (77.4 g) as a crystalline product. 1H NMR (400 MHz, D$_2$O) δ=7.46-7.33 (m, 2H), 7.31-7.25 (m, 3H), 6.23 (s, 1H), 4.40 (s, 2H), 4.32 (br s, 2H), 3.93 (quin, J=8.1 Hz, 1H), 3.84-3.71 (m, 4H), 3.40 (quin, J=4.6 Hz, 1H), 2.90-2.52 (m, 9H), 2.36 -2.19 (m, 2H), 2.09-2.00 (m, 1H), 1.30-1.19 (m, 2H), 1.11 (t, J=7.8 Hz, 3H). The structure was confirmed by X-ray crystallography. See FIG. 2.

Using the appropriate starting material and modifications, the following compounds in Table 2 were synthesized using the synthetic procedures described for Compound 1. Only the 1R,2S isomers are shown in the table in an effort to reduce page length.

TABLE 2

| Compound | Structure/name | 1H NMR | LCMS m/z |
|---|---|---|---|
| 3 | 2-(2-aminoethyl)-N-((1R,2S)-2-((E)-1-phenylbut-1-en-2-yl)cyclopropyl)-2-azaspiro[3.3]heptan-6-amine bis(2,2,2-trifluoroacetate) | $^1$H NMR (400 MHz, DMSO-d$_6$) δ 10.43 (s, 3H), 9.25 (s, 13H), 7.98 (s, 17H), 7.33 (t, J = 7.5 Hz, 15H), 7.28-7.11 (m, 22H), 6.18 (s, 7H), 4.08 (s, 20H), 3.77 (s, 9H), 2.93 (s, 19H), 2.71 (s, 13H), 2.58 (s, 14H), 2.44-2.35 (m, 12H), 2.30-2.16 (m, 17H), 1.95 (s, 8H), 1.25-1.06 (m, 38H). | 326.4 [M + H]$^+$ |

TABLE 2-continued

| Compound | Structure/name | 1H NMR | LCMS m/z |
|---|---|---|---|
| 4 | N-(2-(6-(((1R,2S)-2-((E)-1-phenylbut-1-en-2-yl)cyclopropyl)amino)-2-azaspiro[3.3]heptan-2-yl)ethyl)methanesulfonamide bis(2,2,2-trifluoroacetate) | 1H NMR (400 MHz, DMSO-d6) δ 9.91 (br s, 1H), 9.22 (br s, 2H), 7.35 (t, J = 7.5 Hz, 2H), 7.30 (t, J = 6.0 Hz, 1H), 7.26-7.17 (m, 3H), 6.21 (s, 1H), 4.28-4.19 (m, 1H), 4.19-4.06 (m, 3H), 3.88-3.70 (m, 1H), 3.28-3.20 (m, 2H), 3.20-3.11 (m, 2H), 2.96 (s, 3H). 2.82-2.64 (m, 2H), 2.63-2.52 (m, 1H), 2.47-2.35 (m, 1H), 2.29-2.17 (m, 2H), 2.02-1.89 (m, 1H), 1.17 (t, J =7.3 Hz, 2H), 1.12 (t, J = 7.5 Hz, 3H). | 404.1 [M + H]+ |
| 5 | N-(2-(6-(((1R,2S)-2-((E)-1-phenylbut-1-en-2-yl)cyclopropyl)amino)-2-azaspiro[3.3]heptan-2-yl)ethyl)acetamide bis(2,2,2-trifluoroacetate) | 1H NMR (400 MHz, DMSO-d6) δ 9.81 (br s, 1H), 9.21 (br s, 2H), 8.05 (t, J = 5.6 Hz, 1H), 7.39-7.31 (m, 2H), 7.27-7.17 (m, 3H), 6.21 (s, 1H), 4.27-4.18 (m, 1H), 4.15-4.05 (m, 3H), 3.85-3.74 (m, 1H), 3.26-3.10 (m, 4H), 2.80-2.70 (m, 1H), 2.70-2.63 (m, 1H), 2.63-2.54 (m, 1H), 2.47-2.36 (m, 1H), 2.30-2.18 (m, 2H), 2.00-1.91 (m, 1H), 1.83 (s, 3H), 1.21-1.14 (m, 2H), 1.12 (t, J = 7.5 Hz, 3H). | 368.4 [M + H]+ |
| 6 | N-(2-(6-(((1R,2S)-2-((E)-1-phenylbut-1-en-2-yl)cyclopropyl)amino)-2-azaspiro[3.3]heptan-2-yl)ethyl)cyclopropanesulfonamide bis(2,2,2-trifluoroacetate) | 1H NMR (400 MHz, DMSO-d6) δ 9.91 (br s, 1H), 9.20 (br s, 2H), 7.42-7.31 (m, 3H), 7.28-7.16 (m, 3H), 6.21 (s, 1H), 4.27-4.19 (m, 1H), 4.19-4.15 (m, 1H), 4.15-4.06 (m, 2H), 3.87-3.72 (m, 1H), 3.27-3.14 (m, 4H), 2.81-2.66 (m, 2H), 2.66-2.60 (m, 1H), 2.60-2.52 (m, 1H), 2.47-2.35 (m, 1H), 2.30-2.17 (m, 2H), 2.01-1.91 (m, 1H), 1.21-1.15 (m, 2H), 1.12 (t, J = 7.5 Hz, 3H), 1.04-0.95 (m, 2H), 0.95-0.87 (m, 2H). | 430.4 [M + H]+ |

TABLE 2-continued

| Compound | Structure/name | 1H NMR | LCMS m/z |
|---|---|---|---|
| 7 | N-(2-(6-(((1R,2S)-2-((E)-1-phenylbut-1-en-2-yl)cyclopropyl)amino)-2-azaspiro[3.3]heptan-2-yl)ethyl)ethanesulfonamide bis(2,2,2-trifluoroacetate) | 1H NMR (400 MHz, DMSO-d6) δ 9.92 (br s, 1H), 9.22 (br s, 2H), 7.40-7.29 (m, 3H), 7.29-7.15 (m, 3H), 6.21 (s, 1H), 4.28-4.19 (m, 1H), 4.19-4.03 (m, 3H), 3.79 (br s, 1H), 3.26-3.17 (m, 2H), 3.16-3.10 (m, 2H), 3.07 (q, J = 7.4 Hz, 2H), 2.80-2.64 (m, 2H), 2.64-2.52 (m, 1H), 2.47-2.35 (m, 1H), 2.31-2.17 (m, 2H), 2.03-1.90 (m, 1H), 1.19 (t, J = 7.4 Hz, 3H), 1.17-1.15 (m, 2H), 1.12 (t, J = 7.5 Hz, 3H). | 418.1 [M + H]+ |
| 8 | N-(2-(6-(((1R,2S)-2-((E)-1-phenylbut-1-en-2-yl)cyclopropyl)amino)-2-azaspiro[3.3]heptan-2-yl)ethyl)propane-2-sulfonamide bis(2,2,2-trifluoroacetate) | 1H NMR (400 MHz, DMSO-d6) δ 9.93 (br s, 1H), 9.25 (br s, 2H), 7.40-7.28 (m, 3H), 7.27-7.15 (m, 3H), 6.21 (s, 1H), 4.28-4.20 (m, 1H), 4.20-4.06 (m, 3H), 3.86-3.73 (m, 1H), 3.26 (dd, J = 13.4, 6.6 Hz, 1H), 3.23-3.09 (m, 4H), 2.80-2.64 (m, 2H), 2.64-2.53 (m, 1H), 2.48-2.36 (m, 1H), 2.32-2.17 (m, 2H), 2.03-1.92 (m, 1H), 1.22 (d, J = 6.8 Hz, 6H), 1.20-1.15 (m, J = 12.4, 5.3 Hz, 2H), 1.12 (t, J = 7.5 Hz, 3H). | 432.2 [M + H]+ |
| 9 | 2-methoxy-N-(2-(6-(((1R,2S)-2-((E)-1-phenylbut-1-en-2-yl)cyclopropyl)amino)-2-azaspiro[3.3]heptan-2-yl)ethyl)ethanesulfonamide bis(2,2,2-trifluoroacetate) | 1H NMR (400 MHz, DMSO-d6) δ 9.83 (br s, 1H), 9.15 (brs, 2H), 7.39-7.33 (m, 2H), 7.31 (t, J = 6.1 Hz, 1H), 7.27-7.17 (m, 3H), 6.21 (s, 1H), 4.29-4.19 (m, 1H), 4.19-4.06 (m, 3H), 3.87-3.72 (m, 1H), 3.65 (t, J = 6.0 Hz, 2H), 3.51-3.42 (m, 1H), 3.27 (s, 3H), 3.21 (s, 2H), 3.18-3.08 (m, 2H), 2.81-2.64 (m, 2H), 2.64-2.53 (m, 1H), 2.46-2.35 (m, 1H), 2.29-2.18 (m, 2H), 2.01-1.90 (m, 1H), 1.21-1.15 (m, 2H), 1.12 (t, J = 7.5 Hz, 3H). | 448.3 [M + H]+ |

TABLE 2-continued

| Compound | Structure/name | 1H NMR | LCMS m/z |
|---|---|---|---|
| 10 | 2-(2-(((1R,2S)-2-((E)-1-phenylbut-1-en-2-yl)cyclopropyl)amino)-7-azaspiro[3.3]nonan-7-yl)propane-1,3-diol bis(2,2,2-trifluoroacetate) | ¹H NMR (400 MHz, DMSO-d₆) δ 10.01-9.78 (m, 2H), 9.59 (br s, 1H), 7.37-7.31 (m, 2H), 7.25-7.18 (m, 3H), 6.20 (s, 1H), 5.39 (br s, 2H), 3.89-3.81 (m, 1H), 3.77 (d, J = 4.5 Hz, 4H), 3.44-3.39 (m, 2H), 3.23-3.15 (m, 2H), 3.13-3.05 (m, 1H), 2.69-2.61 (m, 1H), 2.38-2.31 (m, 1H), 2.29-2.20 (m, 3H), 2.19-2.09 (m, 3H), 1.99-1.86 (m, 4H), 1.36-1.27 (m, 1H), 1.17-1.09 (m, 4H). | 385.5 [M + H]⁺ |
| 11 | 2-(2-(((1R,2S)-2-((E)-1-phenylbut-1-en-2-yl)cyclopropyl)amino)-7-azaspiro[3.5]nonan-7-yl)ethanol dihydrochloride | (500 MHz, DMSO-d6) δ 9.89 (br s, 1H), 9.84 (br s, 1H), 9.79 (br s, 1H), 7.37-7.32 (m, 2H), 7.25-7.19 (m, 3H), 6.20 (s, 1H), 5.31 (br s, 1H), 3.89-3.82 (m, 1H), 3.78-3.72 (m, 2H), 3.43-3.37 (m, 2H), 3.14-3.06 (m, 2H), 3.02-2.82 (m, 2H), 2.69-2.62 (m, 1H), 2.38-2.30 (m, 1H), 2.29-2.20 (m, 3H), 2.17-2.09 (m, 3H), 1.97-1.81 (m, 4H), 1.34-1.28 (m, 1H), 1.17-1.09 (m, 4H) | 355.3 [M + H]⁺ |

Compound 12: 2-methyl-1-(6-(((1R,2S)-2-((E)-1-phenylbut-1-en-2-yl)cyclopropyl)amino)-2-azaspiro[3.3]heptan-2-yl)propan-2-ol bis(2,2,2-trifluoroacetate)

Step 1:

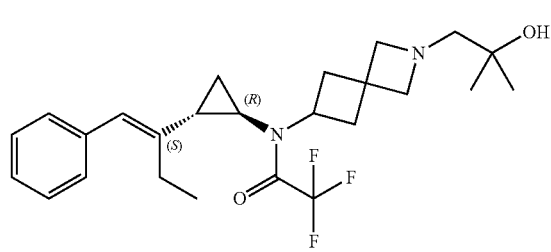

2,2,2-trifluoro-N-(2-(2-hydroxy-2-methylpropyl)-2-azaspiro[3.3]heptan-6-yl)-N-((1R,2S)-2-((E)-1-phenylbut-1-en-2-yl)cyclopropyl)acetamide To a sealed tube was added 2,2,2-trifluoro-N-((1R,2S)-2-(E)-1-phenylbut-1-en-2-yl)cyclopropyl)-N-(2-azaspiro[3.3]heptan-6-yl)acetamide 2,2,2-trifluoroacetate (200 mg, 406 µmol), 2,2-dimethyloxirane (54.0 µL, 609 µmol), diisopropylethylamine (210 µL, 1.21 mmol) and EtOH (4.1 mL). The reaction mixture was stirred at 50° C. for 18 h. The mixture was concentrated under reduced pressure, diluted with ethyl acetate then quenched with 1N HCl. The layers were separated and the aqueous was extracted once with ethyl acetate. The combined organic layer was washed once with brine, dried with sodium sulfate and evaporated under reduced pressure to afford 2,2,2-trifluoro-N-(2-(2-hydroxy-2-methylpropyl)-2-azaspiro[3.3]heptan-6-yl)-N-((1R,2S)-2-((E)-1-phenylbut-1-en-2-yl)cyclopropyl)acetamide yellow oil (296 mg). LCMS m/z 451.3 [M+H]⁺.

Step 2:

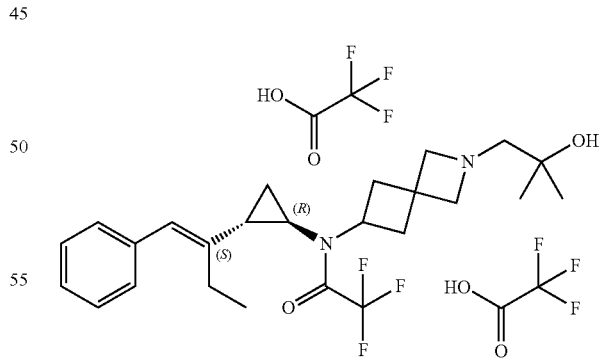

2-methyl-1-(6-(((1R,2S)-2-((E)-1-phenylbut-1-en-2-yl)cyclopropyl)amino)-2-azaspiro[3.3]heptan-2-yl)propan-2-ol bis(2,2,2-trifluoroacetate)

To a solution of 2,2,2-trifluoro-N-(2-(2-hydroxy-2-methylpropyl)-2-azaspiro[3.3]heptan-6-yl)-N-((1R,2S)-2-((E)-1-phenylbut-1-en-2-yl)cyclopropyl)acetamide (250 mg, 554

μmol) in MeOH (2.8 mL) at room temperature was added NaOH (1M, 2.77 mL, 2.77 mmol). The mixture was allowed to stir at room temperature for 60 min. The mixture was quenched with TFA then concentrated under reduced pressure. The crude product was purified on a 30 g C-18 column using McCN/0.1% TFA H2O as eluent with the following gradient (2 CV 0%, 20 CV 0-30%, 3 CV 30%) to afford 2-methyl-1-(6-(((1R,2S)-2-((E)-1-phenylbut-1-en-2-yl)cyclopropyl)amino)-2-azaspiro[3.3]heptan-2-yl)propan-2-ol bis(2,2,2-trifluoroacetate) (22.0 mg) after lyophilisation. LCMS m/z 355.3 [M+H]+. 1H NMR (400 MHz, DMSO-d6) δ 9.59 (br s, 1H), 9.27 (br s, 2H), 7.35 (t, J=7.6 Hz, 2H), 7.29-7.14 (m, 3H), 6.20 (s, 1H), 5.10 (br s, 1H), 4.37-4.25 (m, 1H), 4.25-4.07 (m, 3H), 3.83-3.64 (m, 1H), 3.18-3.09 (m, 2H), 2.79-2.65 (m, 2H), 2.65-2.52 (m, 1H), 2.47-2.33 (m, 1H), 2.30-2.13 (m, 2H), 2.03-1.89 (m, 1H), 1.23-1.15 (m, 2H), 1.13 (s, 6H), 1.11 (t, J=7.6 Hz, 3H).

Using the appropriate starting material and modifications, the following examples in Table 3 were synthesized using the synthetic procedures described for Compound 12. Only the 1R,2S isomers are shown in the table in an effort to reduce page length.

TABLE 3

| Compound | Structure/name | 1H NMR | LCMS m/z |
|---|---|---|---|
| 13 | N-(2-hydroxyethyl)-2-(6-(((1R,2S)-2-((E)-1-phenylbut-1-en-2-yl)cyclopropyl)amino)-2-azaspiro[3.3]heptan-2-yl)acetamide bis(2,2,2-trifluoroacetate) | 1H NMR (400 MHz, DMSO-d6) δ 10.5 (s br, 1H), 9.3 (s br, 2H), 8.46 (s br, 1H), 7.4-7.3 (m, 2H), 7.3-7.2 (m, 3H), 6.20 (s, 1H), 4.79 (s, 1H), 4.23 (s, 1H), 4.2-4.0 (m, 3H), 3.96 (m, 2H), 3.76 (s, 1H), 3.15 (2H), 2.72-2.68 (m, 2H), 2.58 (m, 1H), 2.43 (m, 1H), 2.24 (m, 2H), 1.96 (m, 1H), 1.12 (m, 5H) | 384.2 [M + H]+ |
| 14 | 2-methyl-2-(6-(((1R,2S)-2-((E)-1-phenylbut-1-en-2-yl)cyclopropyl)amino)-2-azaspiro[3.3]heptan-2-yl)propanamide bis(2,2,2-trifluoroacetate) | 1H NMR (400 MHz, DMSO-d6) δ 10.51 (s br, 1H), 9.44 (s br, 2H), 8.79 (s br, 1H), 7.75 (d, J = 59.3 Hz, 2H), 7.35 (d, J = 7.6 Hz, 2H), 7.28-7.14 (m, 3H), 6.20 (s, 1H), 4.20 (d, J = 14.2 Hz, 1H), 4.04 (dd, J = 12.5, 6.9 Hz, 1H), 3.92 (dd, J = 12.1, 6.4 Hz, 1H), 3.76 (s, 1H), 2.72 (s, 1H), 2.58 (ddd, J = 16.3, 12.1, 6.0 Hz, 2H), 2.47-2.35 (m, 1H), 2.30-2.16 (m, 2H), 1.98 (s, 1H), 1.42 (s, 6H), 1.29-1.05 (m, 5H). | 368.7 [M + H]+ |

TABLE 3-continued

| Compound | Structure/name | 1H NMR | LCMS m/z |
|---|---|---|---|
| 15 | N-(2-methyl-1-(6-(((1R,2S)-2-((E)-1-phenylbut-1-en-2-yl)cyclopropyl)amino)-2-azaspiro[3.3]heptan-2-yl)propan-2-yl)methanesulfonamide bis(2,2,2-trifluoroacetate) | 1H NMR (400 MHz, DMSO-d6) δ 9.54 (s, 1H), 9.18 (br s, 2H), 7.39-7.32 (m, 2H), 7.27-7.17 (m, 3H), 7.15 (s, 1H), 6.21 (s, 1H), 4.41-4.30 (m, 1H), 4.30-4.17 (m, 3H), 3.87-3.70 (m, 1H), 3.20 (s, 2H), 3.03 (s, 3H), 2.81-2.65 (m, 3H), 2.64-2.52 (m, 1H), 2.48-2.35 (m, 2H), 2.31-2.16 (m, 2H), 1.97 (s, 1H), 1.29 (s, 3H), 1.21-1.15 (m, 2H), 1.12 (t, J = 7.5 Hz, 3H). | 432.2 [M + H]+ |
| 16 | (R)-1-(2-(((1R,2S)-2-((E)-1-phenylbut-1-en-2-yl)cyclopropyl)amino)-7-azaspiro[3.5]nonan-7-yl)propan-2-ol dihydrochloride | (400 MHz, DMSO-d6) δ 9.99-9.76 (m, 2H), 9.52 (br s, 1H), 7.37-7.32 (m, 2H), 7.25-7.18 (m, 3H), 6.20 (s, 1H), 5.46 (d, J = 4.2 Hz, 1H), 4.17-4.08 (m, 1H), 3.89-3.80 (m, 1H), 3.44-3.37 (m, 2H), 3.09-3.01 (m, 1H), 2.99-2.84 (m, 3H), 2.69-2.62 (m, 1H), 2.37-2.29 (m, 1H), 2.29-2.20 (m, 3H), 2.18-2.09 (m, 3H), 1.96-1.83 (m, 4H), 1.35-1.27 (m, 1H), 1.16-1.07 (m, 7H) | 369.3 [M + H]+ |
| 17 | 7-(2-methoxyethyl)-N-(((1R,2S)-2-((E)-1-phenylbut-1-en-2-yl)cyclopropyl)-7-azaspiro[3.5]nonan-2-amine dihydrochloride | (400 MHz, DMSO-d6) δ 10.02 (br s, 1H), 9.95-9.79 (m, 2H), 7.37-7.31 (m, 2H), 7.25-7.18 (m, 3H), 6.20 (s, 1H), 3.89-3.81 (m, 1H), 3.69 (t, J = 4.9 Hz, 2H), 3.37-3.31 (m, 2H), 3.30 (s, 3H), 3.25-3.18 (m, 2H), 3.03-2.92 (m, 1H), 2.92-2.80 (m, 1H), 2.70-2.61 (m, 1H), 2.37-2.29 (m, 1H), 2.29-2.19 (m, 3H), 2.19-2.08 (m, 3H), 1.97-1.80 (m, 4H), 1.35-1.27 (m, 1H), 1.17-1.09 (m, 4H) | 369.3 [M + H]+ |
| 18 | 2-methyl-1-(2-(((1R,2S)-2-((E)-1-phenylbut-1-en-2-yl)cyclopropyl)amino)-7-azaspiro[3.5]nonan-7-yl)propan-2-ol dihydrochloride | (400 MHz, DMSO-d6) δ 9.96-9.82 (m, 2H), 9.11 (br s, 1H), 7.38-7.32 (m, 2H), 7.25-7.18 (m, 3H), 6.20 (s, 1H), 5.26 (s, 1H), 3.89-3.81 (m, 1H), 3.45-3.38 (m, 2H), 3.09-3.03 (m, 3H), 3.01-2.94 (m, 1H), 2.69-2.62 (m, 1H), 2.35-2.21 (m, 4H), 2.18-2.10 (m, 3H), 2.05-1.94 (m, 2H), 1.92-1.82 (m, 2H), 1.35-1.27 (m, 1H), 1.25 (s, 6H), 1.17-1.10 (m, 4H) | 383.3 [M + H]+ |

TABLE 3-continued

| Compound | Structure/name | 1H NMR | LCMS m/z |
|---|---|---|---|
| 19 | 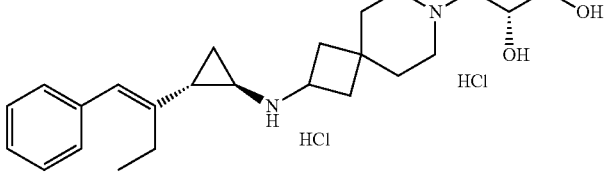<br>(R)-3-(2-(((1R,2S)-2-((E)-1-phenylbut-1-en-2-yl)cyclopropyl)amino)-7-azaspiro[3.5]nonan-7-yl)propane-1,2-diol dihydrochloride | 1H NMR (400 MHz, DMSO-d6) δ 9.90 (br. s., 2 H), 9.58 (br. s., 1 H), 7.43-7.14 (m, 5 H), 6.19 (s, 1 H), 5.54 (br. s., 1 H), 4.98 (br. s., 1 H), 4.03-3.77 (m, 2 H), 3.16 (d, J = 7.0 Hz, 1 H), 2.95 (dd, J = 9.8, 13.5 Hz, 3 H), 2.64 (br. s., 1 H), 2.40-2.06 (m, 7 H), 2.01-1.71 (m, 4 H), 1.38-1.25 (m, 1 H), 1.13 (s, 4 H) | 385.3 [M + H]+ |
| 20 | 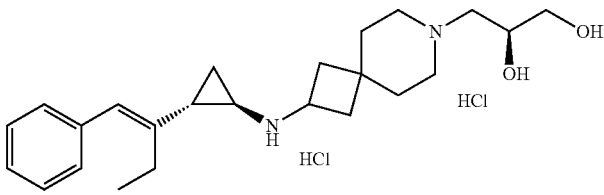<br>(S)-3-(2-(((1R,2S)-2-((E)-1-phenylbut-1-en-2-yl)cyclopropyl)amino)-7-azaspiro[3.5]nonan-7-yl)propane-1,2-diol dihydrochloride | 1H NMR (400 MHz, DMSO-d6) δ 10.06-9.79 (m, 2 H), 9.60 (br. s., 1 H), 7.45-7.30 (m, 2 H), 7.26-7.15 (m, 3 H), 6.19 (s, 1 H), 5.55 (br. s., 1H), 4.99 (br. s., 1H), 3.95 (br. s., 1 H), 3.84 (d, J = 5.5 Hz, 2 H), 3.38-3.24 (m, 2 H), 3.22-3.10 (m, 1 H), 3.05-2.77 (m, 2 H), 2.65 (br. s., 1 H), 2.33 (br. s., 1 H), 2.29-2.19 (m, 2H), 2.19-2.06 (m, 4 H), 2.01-1.76 (m, 4 H), 1.38-1.24 (m, 1 H), 1.19-1.04 (m, 4 H) | 385.3 [M + H]+ |

Compound 21: 2-(6-(((1R,2S)-2-((E)-1-phenylbut-1-en-2-yl)cyclopropyl)amino)-2-azaspiro[3.3]heptan-2-yl)ethanesulfonamide Step 1:

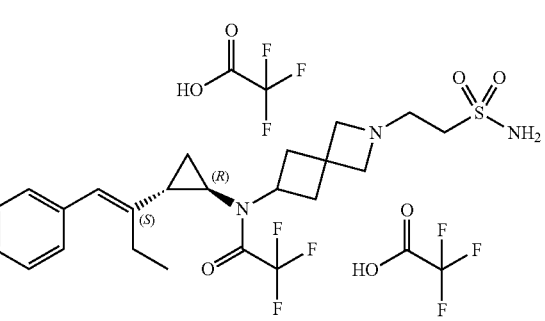

2-(((6-(1R,2S)-2-(E)-1-phenylbut-1-en-2-yl)cyclopropyl)amino)-2-azaspiro[3.3]heptan-2-yl)ethanesulfonamide To a sealed vial charged with 2,2,2-trifluoro-N-(2-(2-hydroxy-2-methylpropyl)-2-azaspiro[3.3]heptan-6-yl)-N-((1R,2S)-2-((E)-1-phenylbut-1-en-2-yl)cyclopropyl)acetamide (0.1610 g, 326 μmol) N,N-dimethylformamide, and sodium carbonate (100 mg, 943 mol) was added ethenesulfonamide (80.1 mg, 748 μmol) at room temperature. The vial was then sealed and heated to 60° C. in an oil bath overnight. The crude mixture was partitioned between 2-methyltetrahydrofuran and water. The organic phase was washed twice with water/brine (1:1 v/v), dried over sodium sulfate and evaporated under vacuum to afford crude 2-(6-(((1R,2S)-2-((E)-1-phenylbut-1-en-2-yl)cyclopropyl)amino)-2-azaspiro[3.3]heptan-2-yl)ethanesulfonamide The crude product was used without further purification. LCMS (ESI) m/z: 485.9 [M+H]+.

Step 2:

Compound 32: 2-(6-(((1R,2S)-2-((E)-1-phenylbut-1-en-2-yl)cyclopropyl)amino)-2-azaspiro[3.3]heptan-2-yl)ethanesulfonamide bis(2,2,2-trifluoroacetate)

Crude 2-(6-(((1R,2S)-2-((E)-1-phenylbut-1-en-2-yl)cyclopropyl)amino)-2-azaspiro[3.3]heptan-2-yl)ethanesulfonamide was dissolved in methanol (2.0 mL) and treated with 10% NaOH aqueous (0.5 mL) at 0° C. for 30 min. The reaction mixture was purified by reverse phase column chromatography 10-30% MeCN/0.1% aqueous TFA as eluent. The pure fractions were combined, frozen and lyophilized over three days. The desired product 2-(6-(((1R,2S)-2-((E)-1-phenylbut-1-en-2-yl)cyclopropyl)amino)-2- azaspiro[3.3]heptan-2-yl)ethanesulfonamide bis(2,2,2 trifluoroacetate) was obtained as a white amorphous solid (49.6 mg). LCMS (ESI) m/z: 390.2 [M+H]+. 1H NMR (500 MHz, MeOD) δ 7.34-7.28 (m, 2H), 7.23-7.15 (m, 3H), 6.26 (s, 1H), 4.36 (s, 2H), 4.27 (s, 2H), 3.92 (p, J=8.1 Hz, 1H), 3.67 (t, J=6.7 Hz, 2H), 3.41 (t, J=6.7 Hz, 2H), 2.88-2.79 (m, 2H), 2.79-2.72 (m, 1H), 2.67-2.56 (m, 2H), 2.40-2.25 (m, 2H), 2.09-2.01 (m, 1H), 1.40 (s, 2H), 1.33-1.20 (m, 3H), 1.17 (t, J=7.6 Hz, 3H).

Using the appropriate starting material and modifications, the following examples in Table 4 were synthesized using the synthetic procedures described for Compound 21. Only the 1R,2S isomers are shown in the table in an effort to reduce page length.

TABLE 4

| Compound | Structure/name | 1H NMR | LCMS m/z |
|---|---|---|---|
| 22 | 3-(6-(((1R,2S)-2-((E)-1-phenylbut-1-en-2-yl)cyclopropyl)amino)-2-azaspiro[3.3]heptan-2-yl)propanamide bis(2,2,2-trifluoroacetate) | 1H NMR (500 MHz, MeOD) δ 7.35-7.28 (m, 2H), 7.24-7.16 (m, 3H), 6.26 (s, 1H), 4.45-4.12 (m, 4H), 3.97-3.87 (m, 1H), 3.44 (t, J = 6.4 Hz, 2H), 2.92-2.73 (m, 3H), 2.70 (s, 1H), 2.64-2.53 (m, 4H), 2.39-2.25 (m, 2H), 2.09-1.99 (m, 1H), 1.32-1.20 (m, 2H), 1.17 (t, J = 7.6 Hz, 3H). | 354.4 [M + H]+ |
| 23 | 2-(2-(((1R,2S)-2-((E)-1-phenylbut-1-en-2-yl)cyclopropyl)amino)-7-azaspiro[3.5]nonan-7-yl)ethanesulfonamide dihydrochloride | (400 MHz, DMSO-d6) δ 10.73 (br s, 1H), 9.91-9.73 (m, 2H), 7.38-7.32 (m, 2H), 7.25 (br s, 2H), 7.23-7.18 (m, 3H), 6.20 (s, 1H), 3.91-3.82 (m, 1H), 3.62-3.57 (m, 2H), 3.46-3.37 (m, 4H), 3.07-2.98 (m, 1H), 2.94-2.86 (m, 1H), 2.69-2.62 (m, 1H), 2.39-2.30 (m, 1H), 2.29-2.21 (m, 3H), 2.17-2.08 (m, 3H), 1.99-1.79 (m, 4H), 1.34-1.26 (m, 1H), 1.14 (app-t, J = 7.4 Hz, 4H) | 418.2 [M + H]+ |
| 24 | 3-(2-(((1R,2S)-2-((E)-1-phenylbut-1-en-2-yl)cyclopropyl)amino)-7-azaspiro[3.5]nonan-7-yl)propanamide dihydrochloride | 1H NMR (400 MHz, DMSO-d6) δ 10.33-10.17 (m, 1 H), 9.90 (br. s., 2 H), 7.61 (br. s., 1 H), 7.39-7.28 (m, 2 H), 7.28-7.14 (m, 3 H), 7.09 (br. s., 1 H), 6.19 (s, 1 H), 3.84 (br. s., 1 H), 3.34-3.16 (m, 4 H), 2.92 (d, J = 12.3 Hz, 2 H), 2.67-2.55 (m, 3 H), 2.33 (br. s., 1 H), 2.24 (q, J = 7.5 Hz, 2 H), 2.19-2.06 (m, 2 H), 2.00-1.73 (m, 3 H), 1.37-1.27 (m, 1 H), 1.13 (dt, J = 1.3, 7.5 Hz, 4 H) | 382.3 [M + H]+ |

Compound 25: N-ethyl-2-(6-(((1R,2S)-2-((E)-1-phenylbut-1-en-2-yl)cyclopropyl)amino)-2-azaspiro[3.3]heptan-2-yl)acetamide bis(2,2,2-trifluoroacetate)

Step 1:

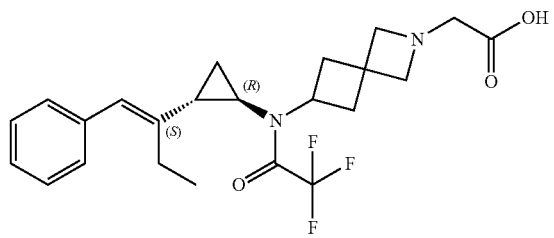

2-(6-(2,2,2-trifluoro-N-((1R,2S)-2-((E)-1-phenylbut-1-en-2-yl)cyclopropyl)acetamido)-2-azaspiro[3.3]heptan-2-yl)acetic acid A solution of 2,2,2-trifluoro-N-(2-(2-hydroxy-2-methylpropyl)-2-azaspiro[3.3]heptan-6-yl)-N-((1R,2S)-2-((E)-1-phenylbut-1-en-2-yl)cyclopropyl)acetamide (800 mg, 1.62 mmol), 2-oxoacetic acid hydrate (298 mg, 3.24 mmol) and 5 drops of AcOH in MeOH (16.2 mL) was treated with sodium cyanoborohydride (305 mg, 4.86 mmol). The reaction mixture was stirred at room temperature for 1 h. After 1 h, additional 2-oxoacetic acid hydrate was added (298 mg, 3.24 mmol) and the reaction was stirred at 45° C. for 1.5 h. The mixture was cooled to room temperature and concentrated under reduced pressure. The residue was diluted with DCM then quenched with sat. NaHCO3. The layers were separated and the aqueous was extracted once with DCM. The combined organic layer was washed once with brine, dried with sodium sulfate and evaporated under reduced pressure to afford crude 2-(6-(2,2,2-trifluoro-N-((1R,2S)-2-((E)-1-phenylbut-1-en-2-yl)cyclopropyl)acetamido)-2-azaspiro[3.3]heptan-2-yl)acetic acid (522 mg). LCMS m/z 437.2 [M+H]⁺.

Step 2:

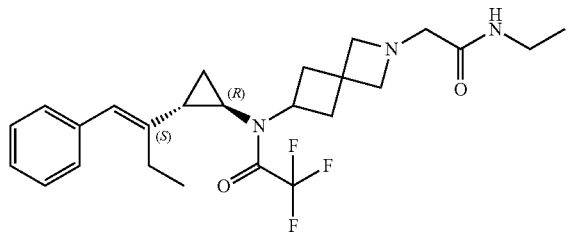

N-(2-(2-(ethylamino)-2-oxoethyl)-2-azaspiro[3.3]heptan-6-yl)-2,2,2-trifluoro-N-((1R,2S)-2-((E)-1-phenylbut-1-en-2-yl)cyclopropyl)acetamide To a solution of 2-(6-(2,2,2-trifluoro-N-((1R,2S)-2-((E)-1-phenylbut-1-en-2-yl)cyclopropyl)acetamido)-2-azaspiro [3.3]heptan-2-yl)acetic acid (175 mg, 400 μmol), ethylammonium chloride (40.4 mg, 496 μmol) and diisopropylethylamine (215 μL, 1.24 mmol) in DMF (2.8 mL) at 0° C. was added HATU (236 mg, 621 μmol). The reaction mixture was allowed to warm and stirred at room temperature for 3 h. The reaction mixture was diluted with water and extracted with ethyl acetate (2×15 mL). The combined organic phase was washed once with brine, dried over anhydrous Na₂SO₄ then concentrated to afford crude N-(2-(2-(ethylamino)-2-oxoethyl)-2-azaspiro[3.3]heptan-6-yl)-2,2,2-trifluoro-N-((1R,2S)-2-((E)-1-phenylbut-1-en-2-yl)cyclopropyl)acetamide (199 mg, 430 μmol) as a yellow oil with residual DMF. LCMS m/z 464.2 [M+H]⁺.

Step 3:

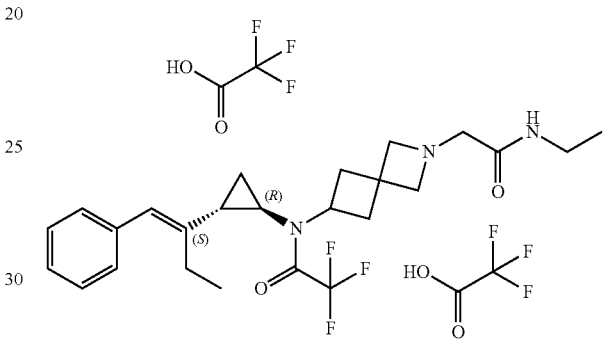

N-ethyl-2-(6-(((1R,2S)-2-((E)-1-phenylbut-1-en-2-yl)cyclopropyl)amino)-2-azaspiro[3.3]heptan-2-yl)acetamide bis(2,2,2-trifluoroacetate)

To a solution of N-(2-(2-(ethylamino)-2-oxoethyl)-2-azaspiro[3.3]heptan-6-yl)-2,2,2-trifluoro-N-((1R,2S)-2-((E)-1-phenylbut-1-en-2-yl)cyclopropyl)acetamide (190 mg, 409 μmol) in MeOH (2.0 mL) at room temperature was added NaOH (1M, 2.04 mL, 2.04 mmol). The mixture was allowed stirred at room temperature for 30 min. The mixture was concentrated under reduced pressure and the crude product was dissolved in TFA/water and purified on a 12 g C-18 column using MeCN/0.1% TFA H2O as eluents with the following gradient (2 CV 0%, 20 CV 0-30%, 5 CV 30%) to afford N-ethyl-2-(6-(((1R,2S)-2-((E)-1-phenylbut-1-en-2-yl)cyclopropyl)amino)-2-azaspiro[3.3]heptan-2-yl)acetamide bis(2,2,2-trifluoroacetate) (86.7 mg) as a white solid after lyophilisation. LCMS m/z 368.1 [M+H]+. 1H NMR (400 MHz, DMSO-d6) δ 10.23 (br s, 1H), 9.23 (br s, 2H), 8.45-8.33 (m, 1H), 7.35 (t, J=7.5 Hz, 2H), 7.27-7.14 (m, 3H), 6.19 (s, 1H), 4.27-4.10 (m, 1H), 4.10-3.99 (m, 2H), 3.98-3.87 (m, 2H), 3.80-3.63 (m, 1H), 3.16-3.04 (m, 2H), 2.77-2.57 (m, 2H), 2.57-2.52 (m, 2H), 2.48-2.35 (m, 2H), 2.30-2.17 (m, 2H), 2.01-1.85 (m, 1H), 1.20-1.14 (m, 2H), 1.12 (t, J=7.5 Hz, 3H), 1.03 (t, J=7.2 Hz, 3H).

Using the appropriate starting material and modifications the following examples in Table 5 were synthesized using the synthetic procedures described for Compound 25. Only the 1R,2S isomers are shown in the table in an effort to reduce page length.

TABLE 5

| Compound | Structure/name | 1H NMR | LCMS m/z |
|---|---|---|---|
| 26 | N-(2-(methylsulfonyl)ethyl)-2-(6-(((1R,2S)-2-((E)-1-phenylbut-1-en-2-yl)cyclopropyl)amino)-2-azaspiro[3.3]heptan-2-yl)acetamide bis(2,2,2-trifluoroacetate) | $^1$H NMR (400 MHz, DMSO-d6) δ 10.26 (br s, 1H), 9.15 (br s, 2H), 8.70 (t, J = 5.7 Hz, 1H), 7.35 (t, J = 7.5 Hz, 2H), 7.27-7.17 (m, 3H), 6.21 (s, 1H), 4.31-4.19 (m, 1H), 4.17-4.12 (m, 1H), 4.12-4.05 (m, 2H), 4.04-3.96 (m, 1H), 3.52 (q, J = 6.5 Hz, 2H), 3.27 (t, J = 6.6 Hz, 2H), 3.02 (s, 3H), 2.75 (s, 1H), 2.71-2.64 (m, 1H), 2.63-2.52 (m, 1H), 2.46-2.34 (m, 2H), 2.29-2.18 (m, 2H), 2.01-1.90 (m, 1H), 1.20-1.14 (m, 2H), 1.12 (t, J = 7.5 Hz, 3H). | 446.3 [M + H]$^+$ |
| 27 | N-isopropyl-2-(6-(((1R,2S)-2-((E)-1-phenylbut-1-en-2-yl)cyclopropyl)amino)-2-azaspiro[3.3]heptan-2-yl)acetamide bis(2,2,2-trifluoroacetate) | $^1$H NMR (400 MHz, DMSO-d6) δ 10.21 (br s, 1H), 9.25 (br s, 2H), 8.31 (d, J = 7.5 Hz, 1H), 7.38-7.32 (m, 2H), 7.26-7.18 (m, 3H), 6.21 (s, 1H), 4.29-4.19 (m, 1H), 4.15-4.11 (m, 1H), 4.11-4.04 (m, 2H), 3.96-3.90 (m, 2H), 3.84 (sept, J = 6.6 Hz, 1H), 3.80-3.70 (m, 1H), 2.79-2.65 (m, 2H), 2.62-2.52 (m, 1H), 2.47-2.35 (m, 1H), 2.28-2.20 (m, 2H), 2.02-1.91 (m, 1H), 1.22-1.14 (m, 2H), 1.12 (t, J = 5.9 Hz, 3H), 1.07 (d, J = 6.6 Hz, 6H). | 382.2 [M + H]$^+$ |
| 28 | N,N-dimethyl-2-(6-(((1R,2S)-2-((E)-1-phenylbut-1-en-2-yl)cyclopropyl)amino)-2-azaspiro[3.3]heptan-2-yl)acetamide bis(2,2,2-trifluoroacetate) | $^1$H NMR (400 MHz, DMSO-d6) δ 10.08 (br s, 1H), 9.16 (br s, 2H), 7.35 (t, J = 7.5 Hz, 2H), 7.27-7.18 (m, 3H), 6.21 (s, 1H), 4.32-4.27 (m, 2H), 4.27-4.23 (m, 1H), 4.18-4.10 (m, 2H), 4.10-4.03 (m, 1H), 3.77 (br s, 1H), 2.87 (d, J = 8.9 Hz, 6H), 2.79-2.71 (m, 1H), 2.71-2.64 (m, 1H), 2.65-2.54 (m, 1H), 2.48-2.35 (m, 1H), 2.29-2.18 (m, 2H), 2.01-1.90 (m, 1H), 1.20-1.15 (m, 2H), 1.12 (t, J = 7.6 Hz, 3H). | 368.1 [M + H]$^+$ |

TABLE 5-continued

| Compound | Structure/name | 1H NMR | LCMS m/z |
|---|---|---|---|
| 29 | N-(methylsulfonyl)-2-(6-(((1R,2S)-2-((E)-1-phenylbut-1-en-2-yl)cyclopropyl)amino)-2-azaspiro[3.3]heptan-2-yl)acetamide bis(2,2,2-trifluoroacetate) | $^1$H NMR (400 MHz, DMSO-d6) δ 10.32 (br s, 1H), 9.18 (br s, 2H), 7.35 (t, J = 7.5 Hz, 2H), 7.29-7.14 (m, 3H), 6.21 (s, 1H), 4.22 (s, 2H), 4.13 (s, 2H), 4.11-4.04 (m, 1H), 3.84-3.71 (m, 1H), 3.18 (d, J = 1.0 Hz, 3H), 2.80-2.70 (m, 1H), 2.70-2.57 (m, 2H), 2.49-2.39 (m, 2H), 2.29-2.17 (m, 2H), 2.02-1.86 (m, 1H), 1.22-1.14 (m, 2H), 1.12 (t, J = 7.5 Hz, 3H). | 418.3 [M + H]$^+$ |
| 30 | 2-(6-(((1R,2S)-2-((E)-1-phenylbut-1-en-2-yl)cyclopropyl)amino)-2-azaspiro[3.3]heptan-2-yl)propanamide bis(2,2,2-trifluoroacetate) | $^1$H NMR (400 MHz, DMSO-d6) δ 10.33 (br s, 1H), 9.28 (br s, 2H), 7.95 (s, 1H), 7.64 (s, 1H), 7.35 (t, J = 7.5 Hz, 2H), 7.29-7.16 (m, 3H), 6.21 (s, 1H), 4.28-4.13 (m, 1H), 4.13-3.88 (m, J = 16.5, 9.8 Hz, 3H), 3.87-3.70 (m, 1H), 2.81-2.63 (m, J = 20.1 Hz, 2H), 2.62-2.52 (m, 1H), 2.46-2.34 (m, J = 8.4 Hz, 1H), 2.29-2.18 (m, 2H), 2.04-1.90 (m, 1H), 1.27 (d, J = 6.8 Hz, 3H), 1.22-1.14 (m, J = 12.7, 5.5 Hz, 2H), 1.12 (t, J = 7.5 Hz, 3H). | 354.2 [M + H]$^+$ |
| 31 | 2,2-dimethyl-3-(6-(((1R,2S)-2-((E)-1-phenylbut-1-en-2-yl)cyclopropyl)amino)-2-azaspiro[3.3]heptan-2-yl)propanamide bis(2,2,2-trifluoroacetate) | $^1$H NMR (400 MHz, dmso) δ 9.39 (br s, 1H), 9.18 (br s, 2H), 7.47 (s, 1H), 7.39-7.32 (m, 2H), 7.30 (s, 1H), 7.27-7.17 (m, 3H), 6.20 (s, 1H), 4.36-4.27 (m, 1H), 4.24-4.08 (m, 3H), 3.82-3.69 (m, 1H), 3.29-3.18 (m, 2H), 2.82-2.64 (m, 2H), 2.64-2.53 (m, 1H), 2.50-2.31 (m, 2H), 2.31-2.17 (m, 2H), 2.06-1.84 (m, 1H), 1.21-1.15 (m, 2H), 1.14 (s, 6H), 1.11 (t, J = 7.6 Hz, 3H). | 382.4 [M + H]$^+$ |

Each of the aforementioned examples can be reproduced to afford the opposite enantiomer (i.e., 1S,2R) using the procedures described above and intermediate (1S,2R)-2-((E)-1-phenylbut-1-en-2-yl)cyclopropan-1-amine (S)-2-hydroxy-2-phenylacetate instead of (1R,2S)-2-((E)-1-phenylbut-1-en-2-yl)cyclopropan-1-amine (S)-2-hydroxy-2-phenylacetate. The structures of these enantiomers are represented in the following table below.

| Structure/name |
|---|
| 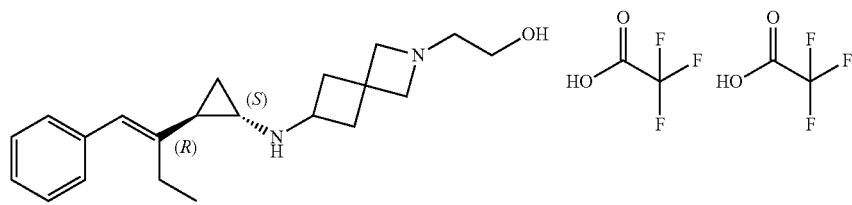<br>2-(6-(((1S,2R)-2-((E)-1-phenylbut-1-en-2-yl)cyclopropyl)amino)-2-azaspiro[3.3]heptan-2-yl)ethanol bis(2,2,2-trifluoroacetate) |
| 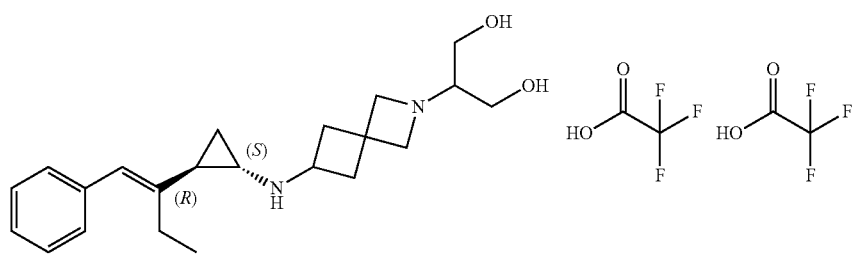<br>2-(6-(((1S,2R)-2-((E)-1-phenylbut-1-en-2-yl)cyclopropyl)amino)-2-azaspiro[3.3]heptan-2-yl)propane-1,3-diol bis(2,2,2-trifluoroacetate) |
| 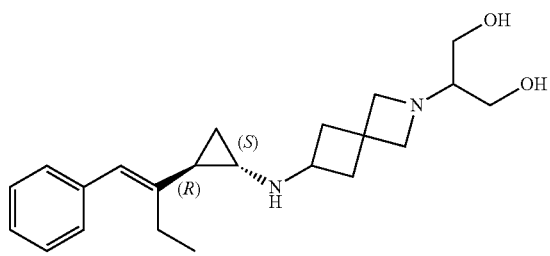<br>2-(6-(((1S,2R)-2-((E)-1-phenylbut-1-en-2-yl)cyclopropyl)amino)-2-azaspiro[3.3]heptan-2-yl)propane-1,3-diol |
| 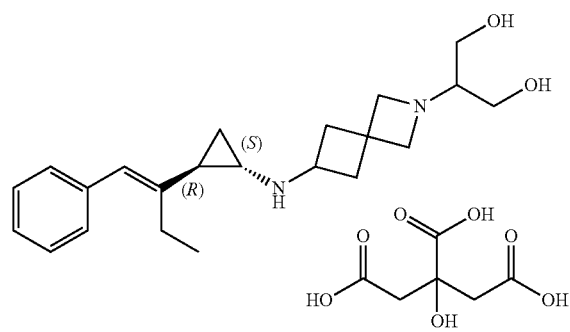<br>2-(6-(((1S,2R)-2-((E)-1-phenylbut-1-en-2-yl)cyclopropyl)amino)-2-azaspiro[3.3]heptan-2-yl)propane-1,3-diol 2-hydroxypropane-1,2,3-tricarboxylate |

| Structure/name |
|---|
| 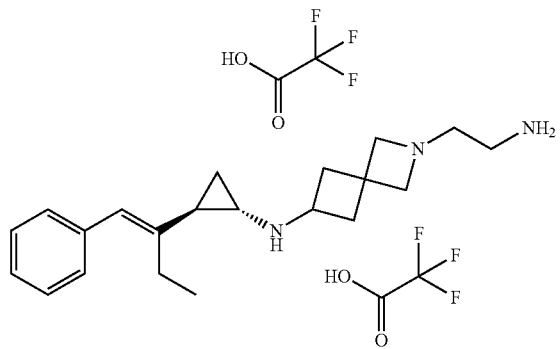
2-(2-aminoethyl)-N-((1S,2R)-2-((E)-1-phenylbut-1-en-2-yl)cyclopropyl)-2-azaspiro[3.3]heptan-6-amine bis(2,2,2-trifluoroacetate) |
| 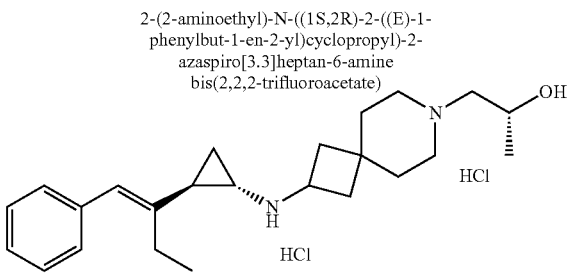
(R)-1-(2-(((1S,2R)-2-((E)-1-phenylbut-1-en-2-yl)cyclopropyl)amino)-7-azaspiro[3.5]nonan-7-yl)propan-2-ol dohydrochloride |
| 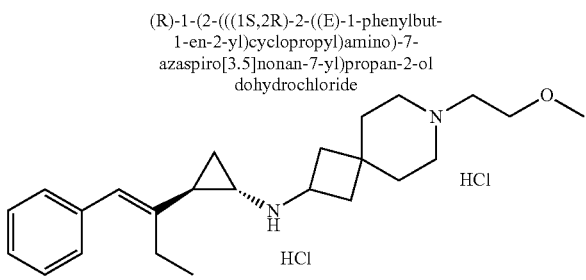
7-(2-methoxyethyl)-N-(((1S,2R)-2-((E)-1-phenylbut-1-en-2-yl)cyclopropyl)-7-azaspiro[3.5]nonan-2-amine dihydrochloride |
| 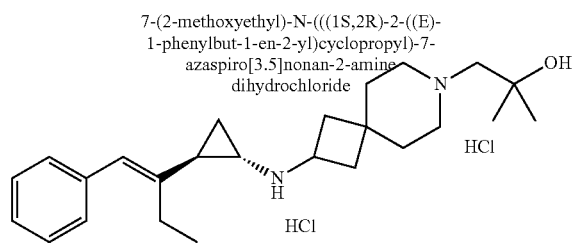
2-methyl-1-(2-(((1S,2R)-2-((E)-1-phenylbut-1-en-2-yl)cyclopropyl)amino)-7-azaspiro[3.5]nonan-7-yl)propan-2-ol dihydrochloride |
| 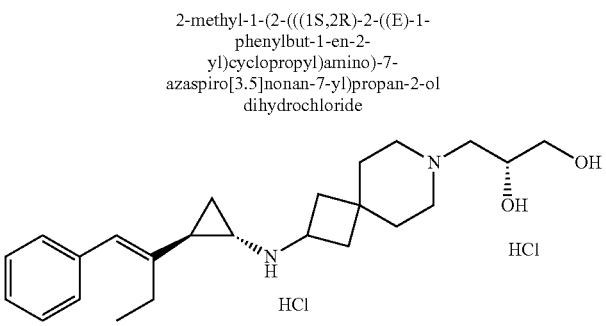
(R)-3-(2-(((1S,2R)-2-((E)-1-phenylbut-1-en-2-yl)cyclopropyl)amino)-7-azaspiro[3.5]nonan-7-yl)propane-1,2-diol dihydrochloride |

-continued

| Structure/name |
|---|

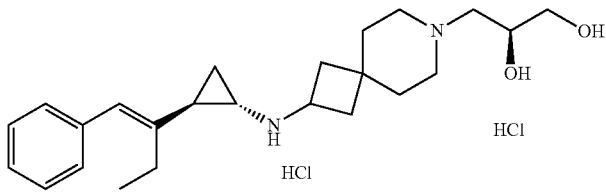 [SMILES: CC/C(=C\c1ccccc1)[C@H]1C[C@@H]1NC1CC2(CCN(C[C@H](O)CO)CC2)C1 ; Cl ; Cl]

(S)-3-(2-(((1S,2R)-2-((E)-1-phenylbut-1-en-2-yl)cyclopropyl)amino)-7-azaspiro[3.3]nonan-7-yl)propane-1,2-diol dihydrochloride

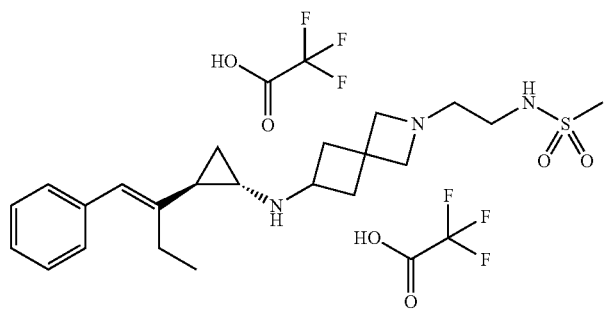

N-2-(6-(((1S,2R)-2-((E)-1-phenylbut-1-en-2-yl)cyclopropyl)amino)-2-azaspiro[3.3]heptan-2-yl)ethyl)merthanesulfonamide bis(2,2,2-trifluoroacetate)

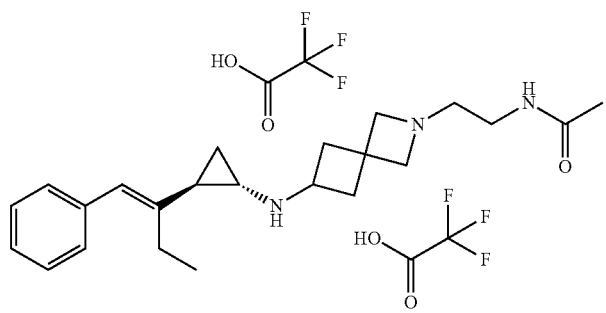

N-(2-(6-(((1S,2R)-2-((E)-1-phenylbut-1-en-2-yl)cyclopropyl)amino)-2-azaspiro[3.3]heptan-2-yl)acetamide bis(2,2,2-trifluoroacetate)

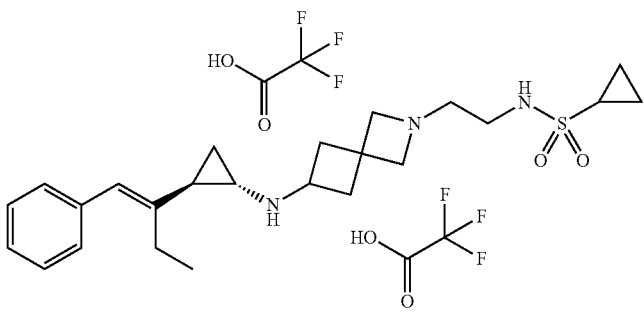

N-(2-(6-(((1S,2R)-2-((E)-1-phenylbut-1-en-2-yl)cyclopropyl)amino)-2-azaspiro[3.3]heptan-2-yl)ethyl)cyclopropanesulfonamide bis(2,2,2-trifluoroacetate)

| Structure/name |
|---|
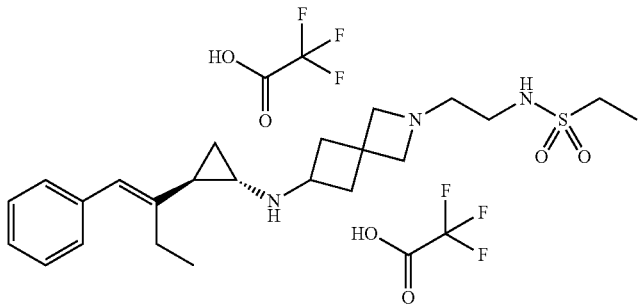
N-2-(6-(((1S,2R)-2-((E)-1-phenylbut-1-en-2-yl)cyclopropyl)amino)-2-azaspiro[3.3]heptan-2-yl)ethyl)ethanesulfonamide bis(2,2,2-trifluoroacetate)
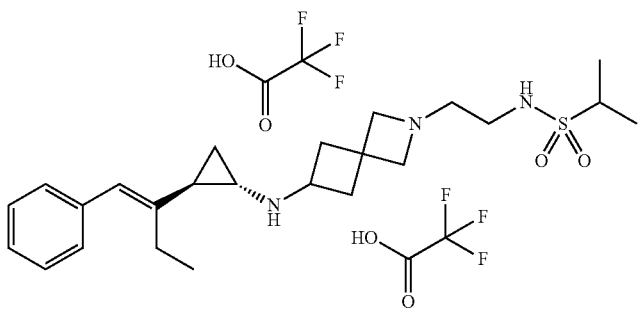
N-2-(6-(((1S,2R)-2-((E)-1-phenylbut-1-en-2-yl)cyclopropyl)amino)-2-azaspiro[3.3]heptan-2-yl)ethyl)propane-2-sulfonamide bis(2,2,2-trifluoroacetate)
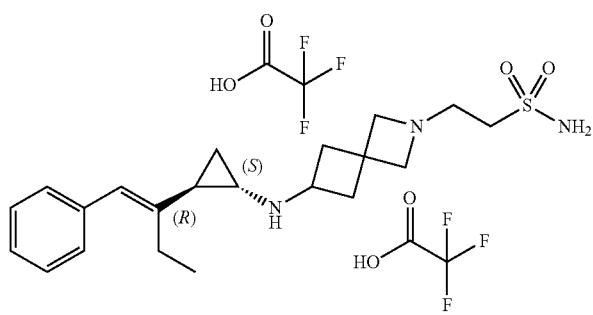
2-(6-(((1S,2R)-2-((E)-1-phenylbut-1-en-2-yl)cyclopropyl)amino)-2-azaspiro[3.3]heptan-2-yl)ethanesulfonamide bis(2,2,2-trifluoroacetate)

| Structure/name |
|---|
| 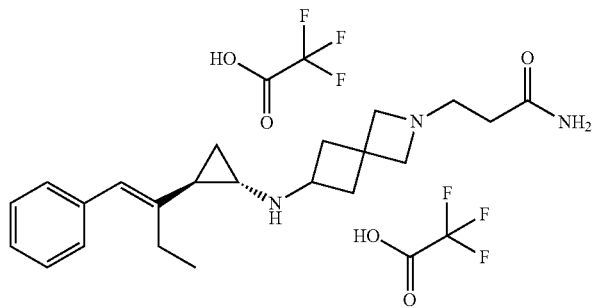<br>3-(6-(((1S,2R)-2-((E)-1-phenylbut-1-en-2-yl)cyclopropyl)amino)-2-azaspiro[3.3]heptan-2-yl)propanamide bis(2,2,2-trifluoroacetate) |
| 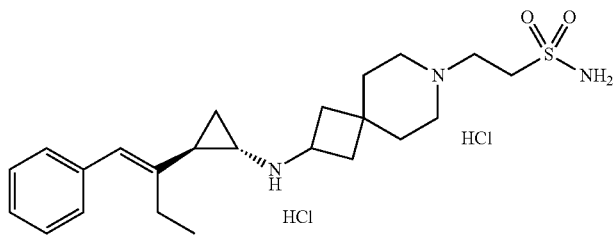 [SMILES: CC/C(=C\c1ccccc1)[C@H]1C[C@@H]1NC1CC2(CCN(CCS(N)(=O)=O)CC2)C1 ; Cl ; Cl]<br>2-(2-(((1S,2R)-2-((E)-1-phenylbut-1-en-2-yl)cyclopropyl)amino)-7-azaspiro[3.5]nonan-7-yl)ethanesulfonamide dihydrochloride |
| 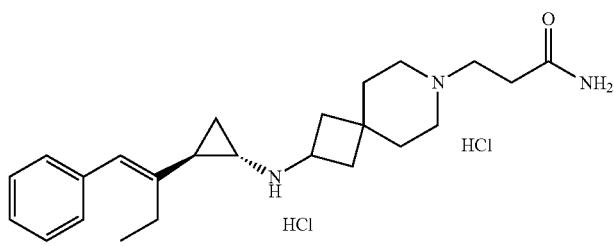 [SMILES: CC/C(=C\c1ccccc1)[C@H]1C[C@@H]1NC1CC2(CCN(CCC(N)=O)CC2)C1 ; Cl ; Cl]<br>3-(2-(((1S,2R)-2-((E)-1-phenylbut-1-en-2-yl)cyclopropyl)amino)-7-azaspiro[3.5]nonan-7-yl)propanamide dihydrochloride |
| 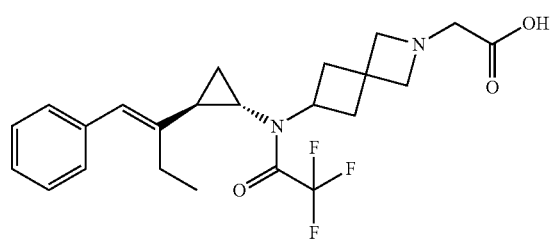 [SMILES: CC/C(=C\c1ccccc1)[C@H]1C[C@@H]1N(C(=O)C(F)(F)F)C1CC2(C1)CN(CC(=O)O)C2]<br>2-(6-(2,2,2-trifluoro-N-((1S,2R)-2-((E)-1-phenylbut-1-en-2-yl)cyclopropyl)acetamido)-2-azaspiro[3.3]heptan-2-yl)acetic acid |

| Structure/name |
|---|
| 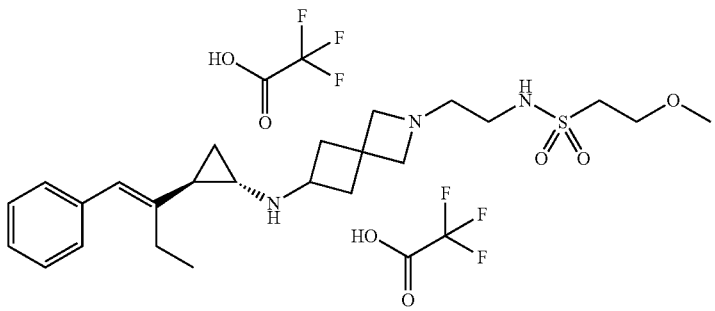<br>2-methoxy-N-2-(6-((((1S,2R)-2-((E)-1-phenylbut-1-en-2-yl)cyclopropyl)amino)-2-azaspiro[3.3]heptan-2-yl)ethyl)ethanesulfonamide bis(2,2,2-trifluoroacetate) |
| 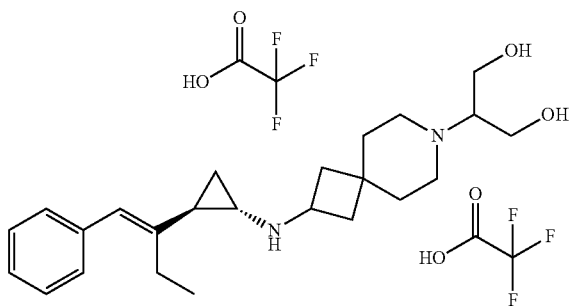<br>2-(2-((((1S,2R)-2-((E)-1-phenylbut-1-en-2-yl)cyclopropyl)amino)-7-azaspiro[3.5]nonan-7-yl)propane-1,3-diol bis(2,2,2-trifluoroacetate) |
| 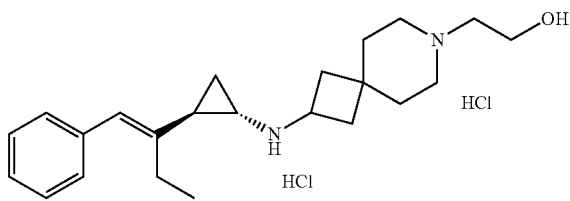 [SMILES: CC/C(=C\c1ccccc1)[C@H]1C[C@@H]1NC1CC2(CCN(CCO)CC2)C1 ; Cl ; Cl]<br>2-(2-((((1S,2R)-2-((E)-1-phenylbut-1-en-2-yl)cyclopropyl)amino)-7-azaspiro[3.5]nonan-7-yl)ethanol dihydrochloride |
| 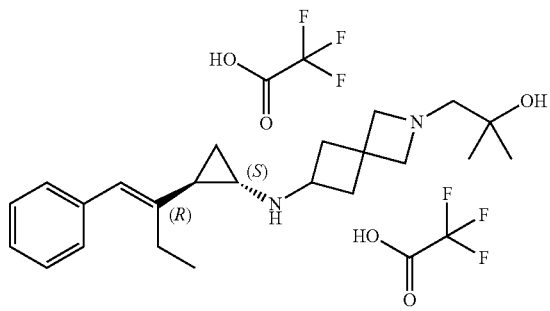<br>2-methyl-1-(6-((((1S,2R)-2-((E)-1-phenylbut-1-en-2-yl)cyclopropyl)amino)-2-azaspiro[3.3]heptan-2-yl)propan-2-ol bis(2,2,2-trifluoroacetate) |

-continued
Structure/name
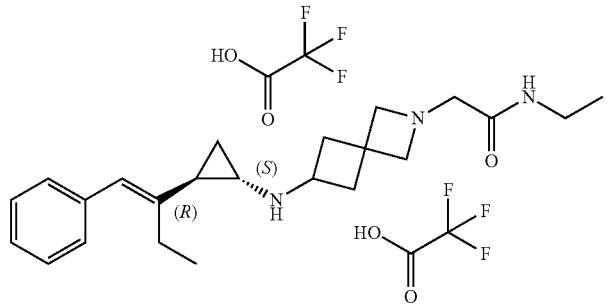
N-ethyl-2-(6-(((1S,2R)-2-((E)-1-
phenylbut-1-en-2-
yl)cyclopropyl)amino)-2-
azaspiro[3.3]heptan-2-yl)acetamide
bis(2,2,2-trifluoroacetate)
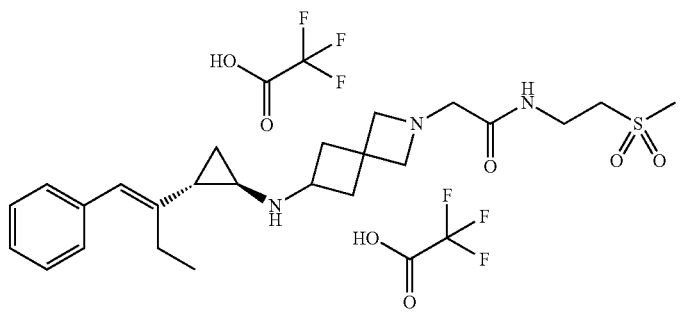
N-(2-(methylsulfonyl)ethyl)-2-(6-
(((1R,2S or 1S,2R)-2-((E)-1-phenylbut-
1-en-2-yl)cyclopropyl)amino)-2-
azaspiro[3.3]heptan-2-yl)acetamide
bis(2,2,2-trifluoroacetate)
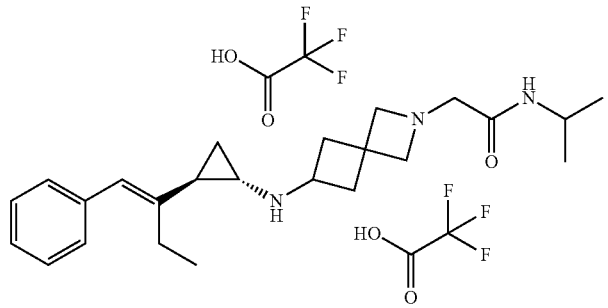
N-isopropyl-2-(6-(((1S,2R)-2-((E)-1-
phenylbut-1-en-2-
yl)cyclopropyl)amino)-2-
azaspiro[3.3]heptan-2-yl)acetamide
bis(2,2,2-trifluoroacetate)

| Structure/name |
|---|
| 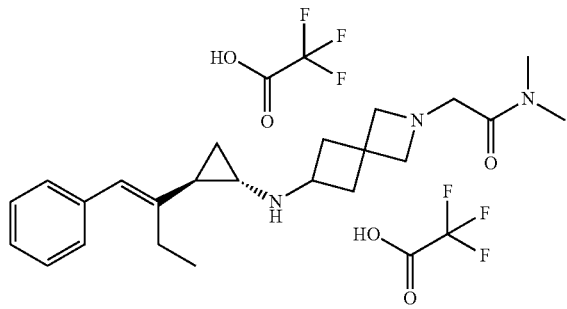<br>N,N-dimethyl-2-(6-(((1S,2R)-2-((E)-1-phenylbut-1-en-2-yl)cyclopropyl)amino)-2-azaspiro[3.3]heptan-2-yl)acetamide bis(2,2,2-trifluoroacetate) |
| 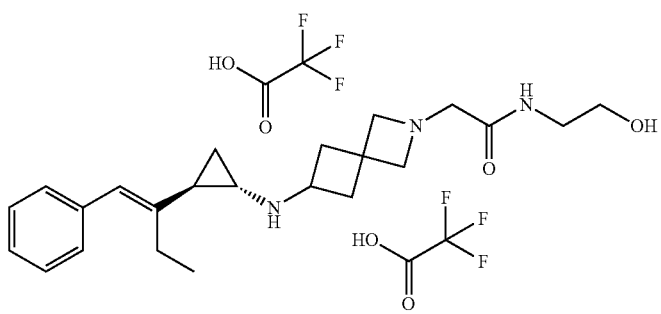<br>N-(2-hydroxyethyl)-2-(6-(((1S,2R)-2-((E)-1-phenylbut-1-en-2-yl)cyclopropyl)amino)-2-azaspiro[3.3]heptan-2-yl)acetamide bis(2,2,2-trifluoroacetate) |
| 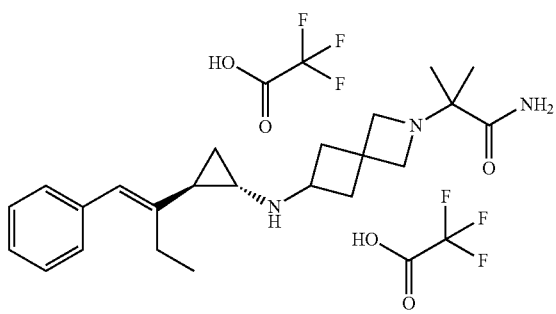<br>2-methyl-2-(6-(((1S,2R)-2-((E)-1-phenylbut-1-en-2-yl)cyclopropyl)amino)-2-azaspiro[3.3]heptan-2-yl)propanamide bis(2,2,2-trifluoroacetate) |

-continued
Structure/name
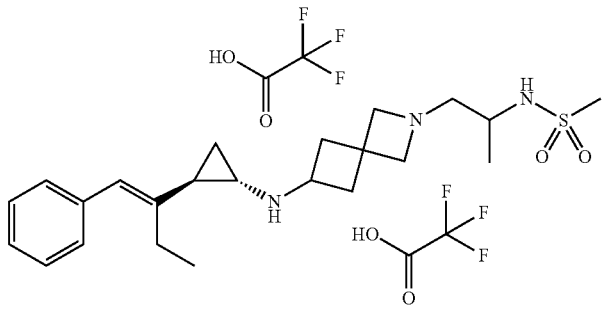
N-(2-methyl-1-(6-((((1S,2R)-2-((E)-1-
phenylbut-1-en-2-yl)cyclopropyl)amino)-
2-azaspiro[3.3]heptan-2-yl)propan-2-
yl)methanesulfonamide bis(2,2,2-
trifluoroacetate)
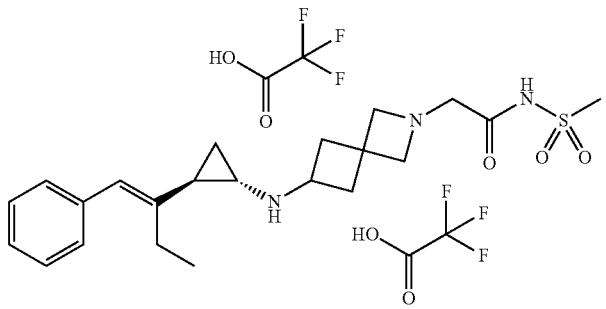
N-(methanesulfonyl)-2-(6-((((1S,2R)-2-
((E)-1-phenylbut-1-en-2-
yl)cyclopropyl)amino)-2-
azaspiro[3.3]heptan-2-yl)acetamide
bis(2,2,2-trifluoroacetate)
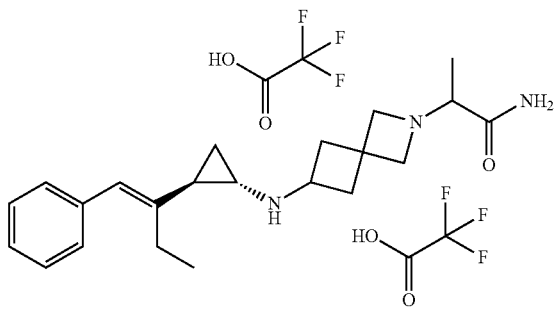
2-(6-((((1S,2R)-2-((E)-1-phenylbut-1-en-
2-yl)cyclopropyl)amino)-2-
azaspiro[3.3]heptan-2-yl)proanamide
bis(2,2,2-trifluoroacetate)

| Structure/name |
|---|
| 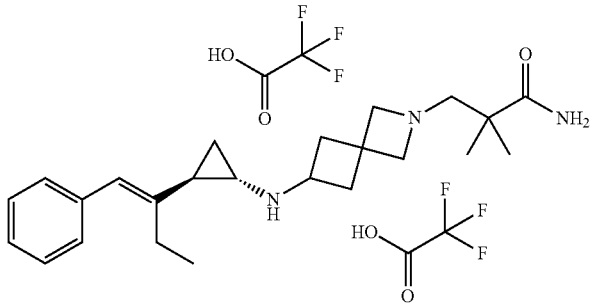<br>2,2-dimethyl-3-(6-(((1S,2R)-2-((E)-1-phenylbut-1-en-2-yl)cyclopropyl)amino)-2-azaspiro[3.3]heptan-2-yl)propanamide bis(2,2,2-trifluoroacetate) |

LSD1 TR-FRET Assay

LSD1 demethylase reactions were carried out in 50 mM HEPES pH 7.4, 100 mM NaCl, 1 mM DTT, 0.01% Tween-20, and 0.1 mg/mL BSA. All enzymatic reactions were performed for 50 minutes at room temperature in a 10-μL volume. Five microliters of 8 μM biotinylated H3K4me1 peptide solution was added to each well of a black 384 well, clear-bottom assay plate containing 80 nL compound (final concentration of 0.8% DMSO and 4 μM substrate). Reactions were initiated by the addition of a mixture containing 20 nM LSD1 and 80 nM FAD (5 μL). LSD1 and FAD final concentrations were 10 and 40 nM, respectively. Enzyme activity was stopped by the addition of 90 μL of high salt buffer consisting of 50 mM HEPES pH 7.4, 500 mM NaCl, 1 mM DTT, 0.01% Tween-20, and 0.1 mg/mL BSA. Ten microliters of the quenched reaction mixtures were transferred to a black 384 well ProxiPlate. Ten microliters of detection mixture was added to the ProxiPlate, Europium-labeled antibody and Streptavidin APC were used at final concentrations of 0.3 nM and 200 nM, respectively (total assay volume of 20 μL). Capture of the product peptide by the anti-H3K4me0 antibody and Streptavidin APC was allowed to proceed for 60 min at room temperature before measuring the TR-FRET signal. Plates were read on a Perkin Elmer EnVision. Percent inhibition was calculated using Max (no inhibitor) and Min (quenched with stop buffer) controls and inhibition curves plotted to determine $IC_{50}$ values.

LSD1 LY96 Quantigene Assay

MV4-11 cells were cultured at a density of 4×104 cells per well in a 96-well plates and treated with various doses inhibitor starting from 10 μM up to 0.0005 μM for 16 h. The LY-96 mRNA induction was quantified using the Quantigene 2.0 system (Affymetrix). The cells were lysed with Lysis Mixture containing Proteinase K. The working reagent for capturing the RNA was prepared according to the steps detailed in "Capturing Target RNA from Cultured Cell or Blood Lysates" in the Quantigene handbook. The subsequent hybridization with LY-96 probe, signal amplification and detection steps were performed as described in the manual. The chemiluminescence was read using Envision (PerkinElmer) and Abase (IDBS software) was used to plot the dose response curves and calculate $IC_{50}$.

Kasumi-1 $GI_{50}$ Assay

Cells were plated at 5,000 cells per well in 96 well tissue culture dishes containing tool compounds arrayed in a 10-point dose curve, ranging from 0 to 10 mM with 4-fold dilutions, and split every fourth day at a fixed ratio to re-establish 5,000 cells/well density for DMSO-treated controls. Cell treatments were carried out for a total of 12 days. At each 4-day split, the viable cell numbers were determined using the Cell Titer-Glo luminescent cell viability assay (Promega, Madison, Wis. USA) using an EnVision® Multilabel Plate Reader (Perkin Elmer, Waltham, Mass. USA). GraphPad Prism 6 (GraphPad Software, Inc., La Jolla, Calif. USA) was used for curve fitting and determination of $GI_{50}$ values.

TABLE 6

| Compound | LSD1 TR-FRET $IC_{50}$ | LSD1 LY96 $EC_{50}$ | Kasumi-1 $GI_{50}$ |
|---|---|---|---|
| 1 | A | A | A |
| 2 | A | A | A |
| 4 | A | A | A |
| 5 | ND | A | A |
| 6 | ND | A | A |
| 7 | ND | A | A |
| 8 | ND | A | A |
| 9 | ND | A | A |
| 10 | ND | A | A |
| 11 | A | A | A |
| 13 | A | A | A |
| 14 | ND | A | A |
| 15 | ND | A | A |
| 16 | ND | A | A |
| 17 | A | A | A |
| 18 | ND | A | A |
| 19 | ND | A | A |
| 20 | ND | A | A |
| 22 | A | A | A |
| 23 | A | A | A |
| 24 | ND | A | A |
| 26 | ND | A | A |
| 27 | ND | A | A |
| 28 | ND | A | A |
| 29 | ND | A | A |

TABLE 6-continued

| Compound | LSD1 TR-FRET IC$_{50}$ | LSD1 LY96 EC$_{50}$ | Kasumi-1 GI$_{50}$ |
|---|---|---|---|
| 30 | ND | A | A |
| 32 | A | A | A |

*IC$_{50}$, EC$_{50}$ and GI$_{50}$ values are reported as follows:
"A" indicates an IC$_{50}$ value of less than 100 nM;
"B" indicates an IC$_{50}$ value of 100 nM to 1 µM;
"C" indicates an IC$_{50}$ value of greater than 1 µM and less than 10 µM for each enzyme;
"D" indicates an IC$_{50}$ value of greater than 10 µM for each enzyme;
"*(X µM)" indicates that no inhibition was observed at the highest concentration (i.e., X µM) of compound tested; and
"ND" is not determined.

The invention claimed is:

1. A compound of the Formula:

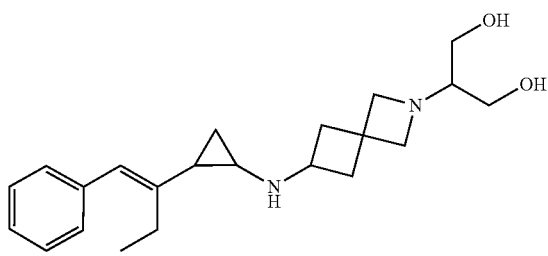 [SMILES: CC/C(=C\c1ccccc1)C1CC1NC1CC2(C1)CN(C(CO)CO)C2]

or a pharmaceutically acceptable salt thereof.

2. The compound of claim 1, wherein the compound is of the Formula:

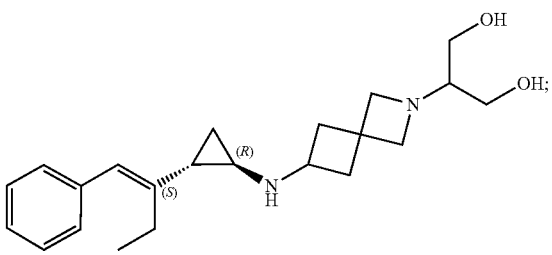

or a pharmaceutically acceptable salt thereof.

3. The compound of claim 2, wherein the enantiomeric purity of the compound is at least 97%.

4. The compound of claim 2, wherein the enantiomeric purity of the compound is at least 98%.

5. The compound of claim 2, wherein the enantiomeric purity of the compound is at least 99%.

6. A pharmaceutical composition comprising an effective amount of a compound of claim 1, or a pharmaceutically acceptable salt thereof; and a pharmaceutically acceptable carrier.

7. A pharmaceutical composition comprising an effective amount of a compound of claim 2, or a pharmaceutically acceptable salt thereof; and a pharmaceutically acceptable carrier.

8. A method of treating a disease that is treatable by inhibiting LSD1 wherein said disease is selected from HIV, prostate cancer, esophageal squamous cell, neuroblastoma, ovarian cancer, bladder cancer, lung cancer, colorectal cancer, squamous cell carcinomas, breast cancer, glioblastoma multiforme, chondrosarcoma, Ewing's sarcoma, osteogenic sarcoma, rhabdomyosarcoma, melanoma, or medulloblastoma comprising the step of administering to a subject in need thereof a compound of claim 1, or a pharmaceutically acceptable salt thereof.

9. A method of treating a disease that is treatable by inhibiting LSD1 wherein said disease is selected from HIV, prostate cancer, esophageal squamous cell, neuroblastoma, ovarian cancer, bladder cancer, lung cancer, colorectal cancer, squamous cell carcinomas, breast cancer, glioblastoma multiforme, chondrosarcoma, Ewing's sarcoma, osteogenic sarcoma, rhabdomyosarcoma, melanoma, or medulloblastoma comprising the step of administering to a subject in need thereof a compound of claim 2, or a pharmaceutically acceptable salt thereof.

10. A compound having the Formula:

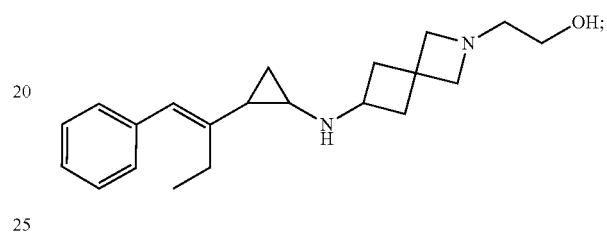

or a pharmaceutically acceptable salt thereof.

11. The compound of claim 10, wherein the compound is of the Formula:

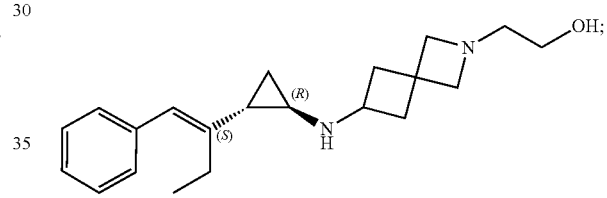

or a pharmaceutically acceptable salt thereof.

12. The compound of claim 11, wherein the enantiomeric purity of the compound is at least 97%.

13. The compound of claim 11, wherein the enantiomeric purity of the compound is at least 98%.

14. The compound of claim 11, wherein the enantiomeric purity of the compound is at least 99%.

15. A pharmaceutical composition comprising an effective amount of a compound of claim 10, or a pharmaceutically acceptable salt thereof; and a pharmaceutically acceptable carrier.

16. A pharmaceutical composition comprising an effective amount of a compound of claim 11, or a pharmaceutically acceptable salt thereof; and a pharmaceutically acceptable carrier.

17. A method of treating a disease that is treatable by inhibiting LSD1 wherein said disease is selected from HIV, prostate cancer, esophageal squamous cell, neuroblastoma, ovarian cancer, bladder cancer, lung cancer, colorectal cancer, squamous cell carcinomas, breast cancer, glioblastoma multiforme, chondrosarcoma, Ewing's sarcoma, osteogenic sarcoma, rhabdomyosarcoma, melanoma, or medulloblastoma comprising the step of administering to a subject in need thereof a compound of claim 10, or a pharmaceutically acceptable salt thereof.

18. A method of treating a disease that is treatable by inhibiting LSD1 wherein said disease is selected from HIV, prostate cancer, esophageal squamous cell, neuroblastoma, ovarian cancer, bladder cancer, lung cancer, colorectal cancer, squamous cell carcinomas, breast cancer, glioblastoma multiforme, chondrosarcoma, Ewing's sarcoma, osteogenic sarcoma, rhabdomyosarcoma, melanoma, or medulloblastoma comprising the step of administering to a subject in need thereof a compound of claim 11, or a pharmaceutically acceptable salt thereof.

\* \* \* \* \*